(12) United States Patent
Bierman et al.

(10) Patent No.: US 9,566,087 B2
(45) Date of Patent: Feb. 14, 2017

(54) VASCULAR ACCESS DEVICE

(71) Applicant: Access Scientific, LLC, San Diego, CA (US)

(72) Inventors: Steven F. Bierman, Del Mar, CA (US); Richard A. Pluth, San Diego, CA (US); Tu Nguyen, Escondido, CA (US)

(73) Assignee: Access Scientific, LLC, San Diego, CA (US)

( * ) Notice: Subject to any disclaimer, the term of this patent is extended or adjusted under 35 U.S.C. 154(b) by 0 days.

(21) Appl. No.: 14/207,120

(22) Filed: Mar. 12, 2014

(65) Prior Publication Data

US 2014/0276432 A1    Sep. 18, 2014

Related U.S. Application Data

(60) Provisional application No. 61/799,992, filed on Mar. 15, 2013.

(51) Int. Cl.
*A61M 5/178* (2006.01)
*A61B 17/34* (2006.01)
(Continued)

(52) U.S. Cl.
CPC ....... *A61B 17/3498* (2013.01); *A61B 17/3415* (2013.01); *A61M 25/0097* (2013.01);
(Continued)

(58) Field of Classification Search
CPC ............ A61B 17/3415; A61B 17/3498; A61M 25/0097; A61M 25/0662; A61M 25/0668
See application file for complete search history.

(56) References Cited

U.S. PATENT DOCUMENTS 3,565,074 A    2/1971 Foti et al.
4,068,659 A    1/1978 Moorehead
(Continued)

FOREIGN PATENT DOCUMENTS

EP    0139091    7/1984
EP    0502714    11/1995
(Continued)

OTHER PUBLICATIONS

Oct. 1, 2014, International Search Report and Written Opinion of Application No. PCT/US14/26803 Filed on Mar. 13, 2014.
(Continued)

*Primary Examiner* — Rebecca E Eisenberg
(74) *Attorney, Agent, or Firm* — Knobbe Martens Olson & Bear, LLP

(57) ABSTRACT

An access device for placing a medical article within a body space includes a needle, a dilator, and a sheath. The dilator can be coaxially and slideably disposed about the needle, and the sheath can be coaxially and slideably disposed about the dilator. The access device can further include a inner member coaxially disposed between the needle and dilator. The needle can include a fenestration in fluid communication with a space between the needle and inner member. When the needle punctures a blood vessel, the fenestration allows blood to flow into the space between the needle and inner member to provide a visual indicator to a physician or healthcare professional that the needle is in a vessel.

23 Claims, 27 Drawing Sheets

(51) Int. Cl.
*A61M 25/06* (2006.01)
*A61M 25/00* (2006.01)

(52) U.S. Cl.
CPC .... *A61M 25/0606* (2013.01); *A61M 25/0662* (2013.01); *A61M 25/0668* (2013.01); *A61M 25/0693* (2013.01); *A61M 2025/0004* (2013.01); *A61M 2025/0006* (2013.01); *A61M 2025/0681* (2013.01)

(56) References Cited

U.S. PATENT DOCUMENTS

| | | |
|---|---|---|
| 4,205,675 A | 6/1980 | Vaillancourt |
| 4,230,123 A | 10/1980 | Hawkins, Jr. |
| 4,417,886 A | 11/1983 | Frankhouser et al. |
| 4,525,157 A | 6/1985 | Vaillancourt |
| 4,581,019 A | 4/1986 | Curelaru et al. |
| 4,610,665 A | 9/1986 | Matsumoto et al. |
| 4,629,450 A | 12/1986 | Suzuki et al. |
| 4,655,750 A | 4/1987 | Vaillancourt |
| 4,661,300 A | 4/1987 | Daugherty |
| 4,791,937 A | 12/1988 | Wang |
| 4,850,975 A | 7/1989 | Furukawa |
| 4,869,259 A | 9/1989 | Elkins |
| 4,894,052 A | 1/1990 | Crawford |
| 4,961,729 A | 10/1990 | Vaillancourt |
| 4,978,334 A | 12/1990 | Toye et al. |
| 5,059,186 A | 10/1991 | Yamamoto et al. |
| 5,066,284 A | 11/1991 | Mersch et al. |
| 5,105,807 A | 4/1992 | Kahn et al. |
| 5,108,374 A | 4/1992 | Lemieux |
| 5,167,637 A | 12/1992 | Okada et al. |
| 5,171,218 A | 12/1992 | Fonger et al. |
| 5,242,410 A | 9/1993 | Melker |
| 5,246,426 A | 9/1993 | Lewis et al. |
| 5,250,038 A | 10/1993 | Melker et al. |
| 5,295,969 A | 3/1994 | Fischell |
| 5,295,970 A | 3/1994 | Clinton et al. |
| 5,306,253 A | 4/1994 | Brimhall |
| 5,312,355 A | 5/1994 | Lee |
| 5,334,157 A | 8/1994 | Klein et al. |
| 5,356,394 A | 10/1994 | Farley et al. |
| 5,366,441 A | 11/1994 | Crawford |
| 5,380,290 A | 1/1995 | Makower et al. |
| 5,397,311 A | 3/1995 | Walker et al. |
| 5,419,766 A | 5/1995 | Chang et al. |
| 5,542,932 A | 8/1996 | Daugherty |
| 5,578,083 A * | 11/1996 | Laguette ............... A61F 2/203 137/855 |
| 5,589,120 A | 12/1996 | Khan et al. |
| 5,676,689 A | 10/1997 | Kensery et al. |
| 5,688,249 A | 11/1997 | Chang et al. |
| 5,704,914 A | 1/1998 | Stocking et al. |
| 5,755,693 A | 5/1998 | Walker et al. |
| 5,795,339 A | 8/1998 | Erskine |
| 5,810,780 A | 9/1998 | Brimhall et al. |
| 5,820,596 A | 10/1998 | Rosen et al. |
| 5,820,606 A * | 10/1998 | Davis ............... A61B 17/3462 604/164.11 |
| 5,827,202 A | 10/1998 | Miraki et al. |
| 5,830,190 A | 11/1998 | Howell |
| 5,833,662 A | 11/1998 | Stevens |
| 5,858,002 A | 1/1999 | Jesch |
| 5,858,007 A | 1/1999 | Fagan et al. |
| 5,873,854 A | 2/1999 | Wolvek |
| 5,885,253 A | 3/1999 | Liu |
| 5,910,132 A | 6/1999 | Schultz |
| 5,935,110 A | 8/1999 | Brimhall |
| 5,951,518 A | 9/1999 | Licata et al. |
| 6,046,143 A | 4/2000 | Khan et al. |
| 6,074,377 A | 6/2000 | Sanfilippo |
| 6,077,249 A | 6/2000 | Dittrich et al. |
| 6,080,141 A | 6/2000 | Castro et al. |
| 6,083,207 A | 7/2000 | Heck |
| 6,120,494 A | 9/2000 | Jonkman |
| 6,179,813 B1 | 1/2001 | Ballow et al. |
| 6,277,100 B1 | 8/2001 | Raulerson |
| 6,436,070 B1 | 8/2002 | Botich et al. |
| 6,461,362 B1 | 10/2002 | Halseth et al. |
| 6,524,277 B1 | 2/2003 | Chang |
| 6,569,120 B1 | 5/2003 | Green et al. |
| 6,607,511 B2 | 8/2003 | Halseth et al. |
| 6,641,564 B1 | 11/2003 | Kraus |
| 6,692,462 B2 | 2/2004 | Mackenzie et al. |
| 6,712,789 B1 | 3/2004 | Lange et al. |
| 6,726,659 B1 | 4/2004 | Stocking et al. |
| 6,783,516 B2 | 8/2004 | O'Heeron |
| 6,808,520 B1 | 10/2004 | Fourkas et al. |
| 6,942,671 B1 | 9/2005 | Smith |
| 6,994,693 B2 | 2/2006 | Tal |
| 7,001,396 B2 | 2/2006 | Glazier et al. |
| 7,025,746 B2 | 4/2006 | Tal |
| 7,083,626 B2 | 8/2006 | Hart et al. |
| 7,101,353 B2 | 9/2006 | Lui et al. |
| 7,163,525 B2 | 1/2007 | Franer |
| 7,192,433 B2 | 3/2007 | Osypka et al. |
| 7,270,649 B2 | 9/2007 | Fitzgerald |
| 7,556,617 B2 | 7/2009 | Voorhees, Jr. et al. |
| 7,717,878 B2 | 5/2010 | Smith |
| 7,722,567 B2 | 5/2010 | Tal |
| 7,744,569 B2 | 6/2010 | Smith |
| 7,922,696 B2 | 4/2011 | Tal et al. |
| 7,972,307 B2 | 7/2011 | Kraus et al. |
| 7,993,305 B2 | 8/2011 | Ye et al. |
| 8,105,286 B2 | 1/2012 | Anderson et al. |
| 8,192,402 B2 | 6/2012 | Anderson et al. |
| 8,202,251 B2 | 6/2012 | Bierman et al. |
| 8,827,958 B2 | 9/2014 | Bierman et al. |
| 2002/0072712 A1 | 6/2002 | Nool et al. |
| 2004/0092879 A1 | 5/2004 | Kraus et al. |
| 2004/0171988 A1 | 9/2004 | Moretti |
| 2004/0267202 A1 | 12/2004 | Potter |
| 2006/0015039 A1 | 1/2006 | Cassidy et al. |
| 2006/0149293 A1 | 7/2006 | King et al. |
| 2007/0123825 A1 | 5/2007 | King et al. |
| 2008/0004569 A1 | 1/2008 | McCrystle et al. |
| 2008/0097386 A1 | 4/2008 | Osypka |
| 2008/0234728 A1 | 9/2008 | Starksen |
| 2008/0262431 A1 | 10/2008 | Anderson et al. |
| 2009/0018508 A1 | 1/2009 | Fisher et al. |
| 2009/0036843 A1 | 2/2009 | Erskine |
| 2009/0177163 A1* | 7/2009 | King ............... A61M 25/0668 604/167.03 |
| 2009/0221961 A1 | 9/2009 | Tal et al. |
| 2009/0227843 A1 | 9/2009 | Smith et al. |
| 2009/0259186 A1* | 10/2009 | Smith ............... A61B 17/3498 604/167.04 |
| 2010/0042049 A1 | 2/2010 | Leeflang et al. |
| 2011/0021994 A1 | 1/2011 | Anderson et al. |
| 2011/0202006 A1 | 8/2011 | Bierman et al. |
| 2011/0218496 A1 | 9/2011 | Bierman |
| 2011/0276002 A1 | 11/2011 | Bierman |
| 2012/0065590 A1 | 3/2012 | Bierman et al. |
| 2012/0316500 A1 | 12/2012 | Bierman et al. |
| 2014/0207069 A1 | 7/2014 | Bierman et al. |
| 2015/0126930 A1 | 5/2015 | Bierman et al. |

FOREIGN PATENT DOCUMENTS

| | | |
|---|---|---|
| EP | 0 904 023 | 3/1999 |
| JP | 08-336593 | 12/1996 |
| JP | 2001-190682 | 7/2001 |
| JP | 2002-172174 | 6/2002 |
| KR | 20050027359 | 3/2005 |
| WO | WO 2008/131289 | 10/2008 |
| WO | WO 2009/114833 | 9/2009 |
| WO | WO 2011/097639 | 8/2011 |
| WO | WO 2012/135764 | 10/2012 |

(56) References Cited

FOREIGN PATENT DOCUMENTS

WO    WO 2012/162677    11/2012
WO    WO 2013/026045    2/2013

OTHER PUBLICATIONS

A photograph of various access devices.
Arrow Trauma Products No. TRM-C 12/00 11M, Arrow International, dated 2000.
International Search Report and Written Opinion PCT/US2010/034609, mailed on Jan. 18, 2011.
Photos of a peripheral emergency infusion device Applicant believes to be produced by Arrow International Inc.
Photos of a splittable catheter design.
Photos of an infusion device Applicant believes to be produced by B. Braun Medical Inc.
Oct. 29, 2012, Extended European Search Report, European Patent Application No. 10775500.1 filed May 12, 2010.
Nov. 16, 2012, International Search Report and Written Opinion for PCT Application No. PCT/US2012/051495 filed Aug. 17, 2012.

\* cited by examiner

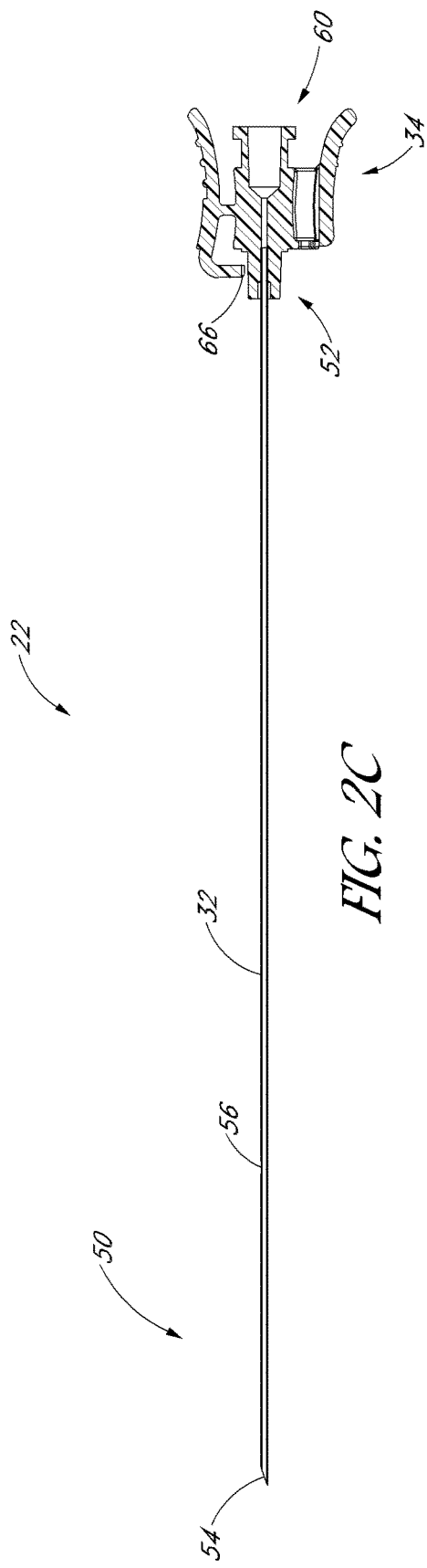
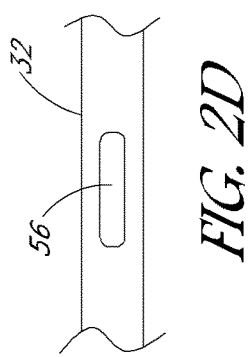
FIG. 2C
FIG. 2D

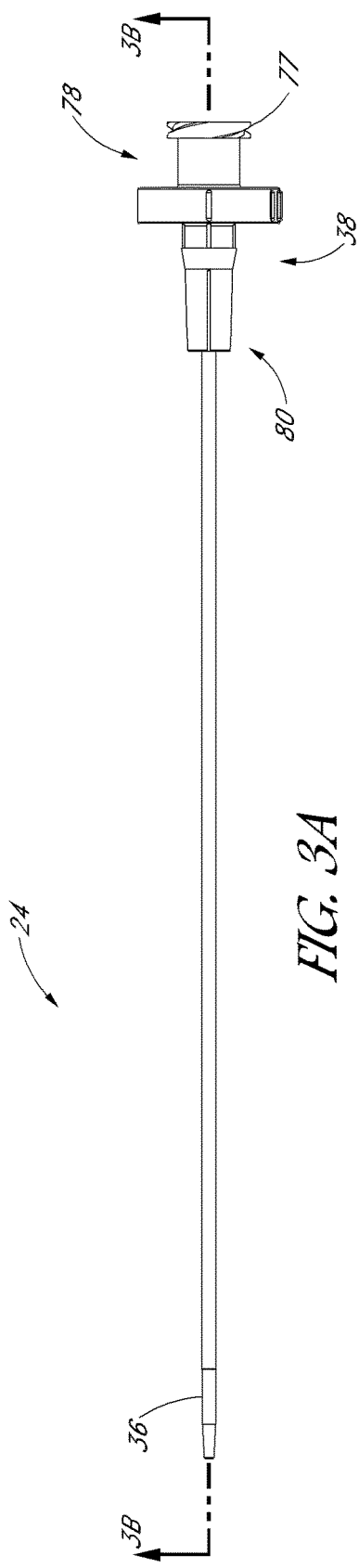
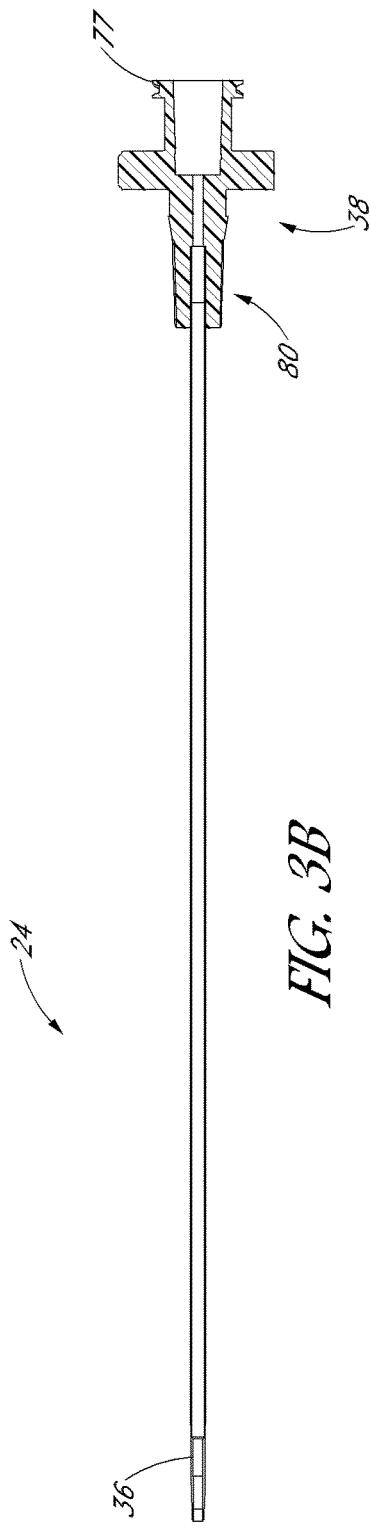
FIG. 3A
FIG. 3B

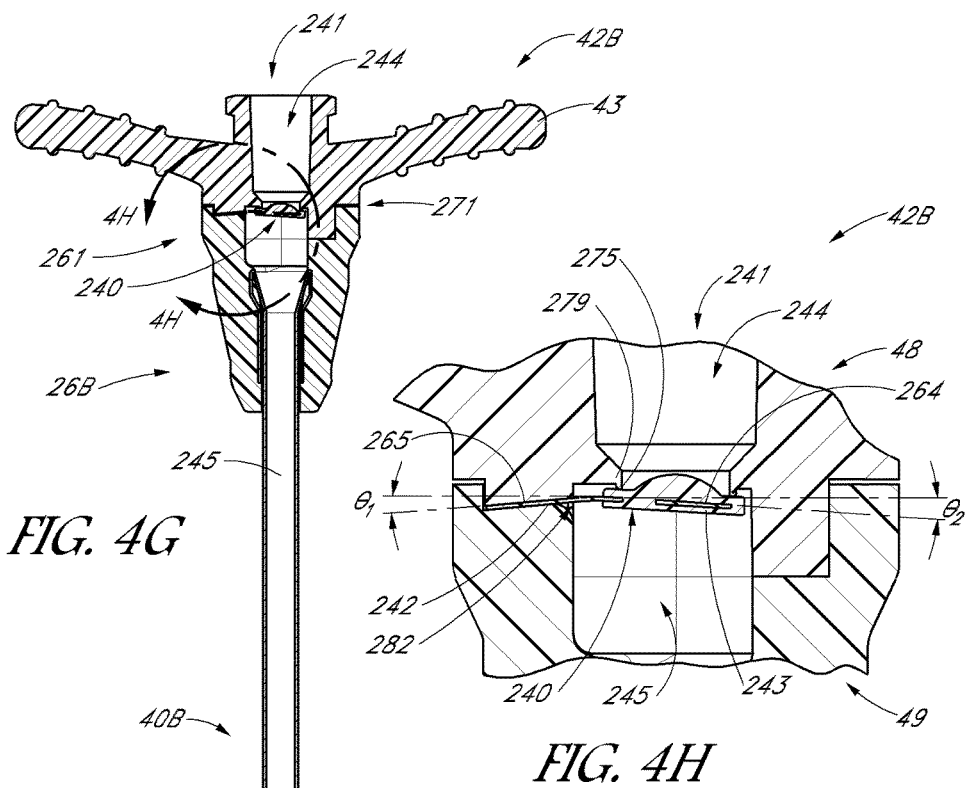
FIG. 4G
FIG. 4H
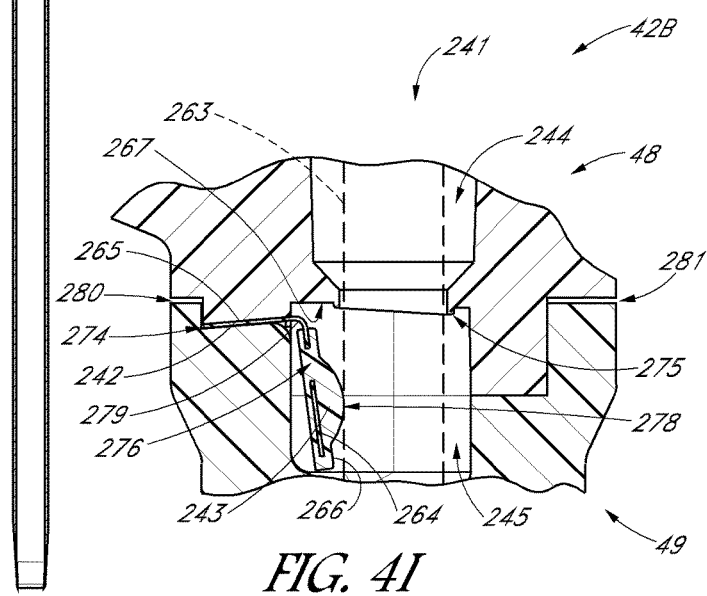
FIG. 4I

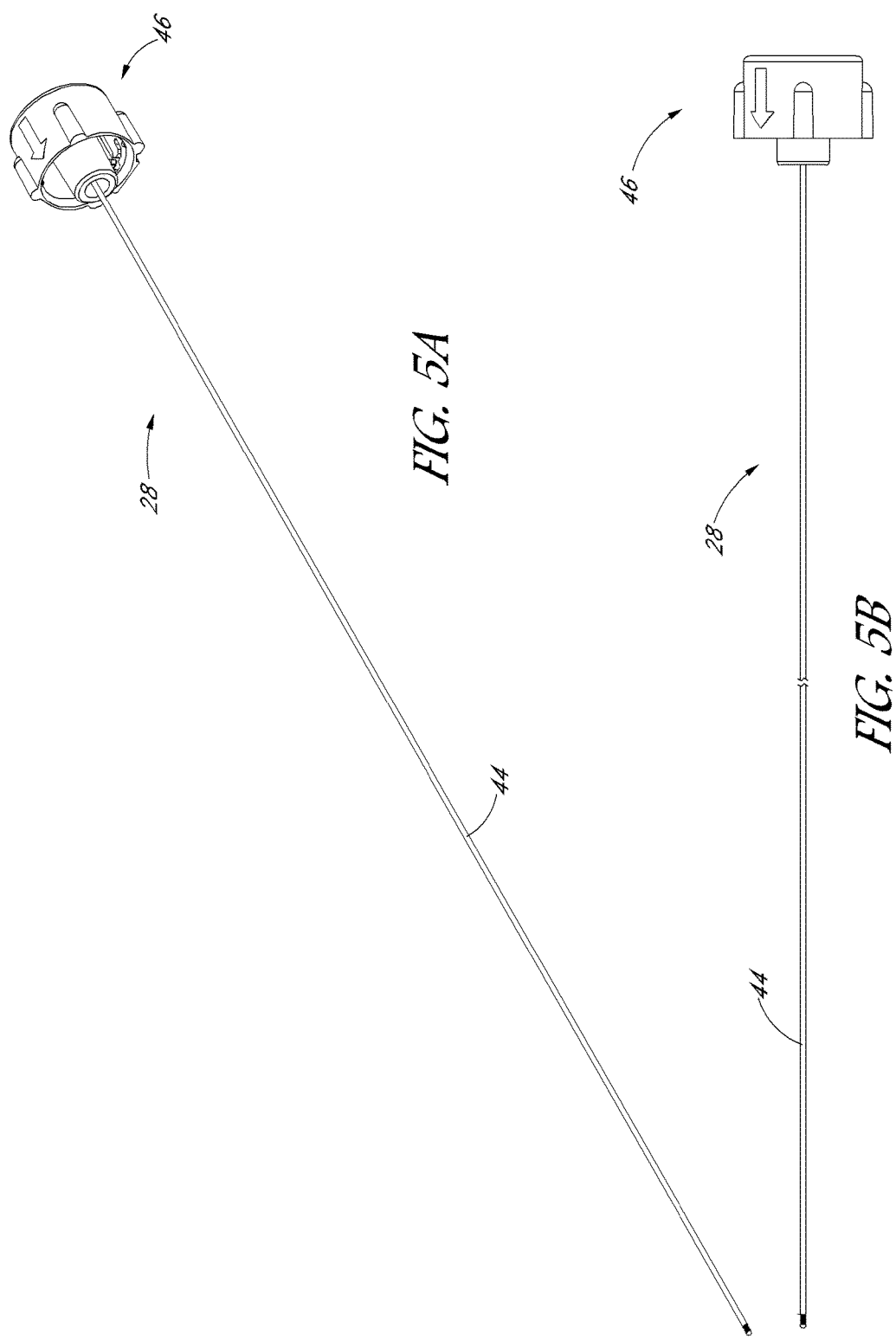

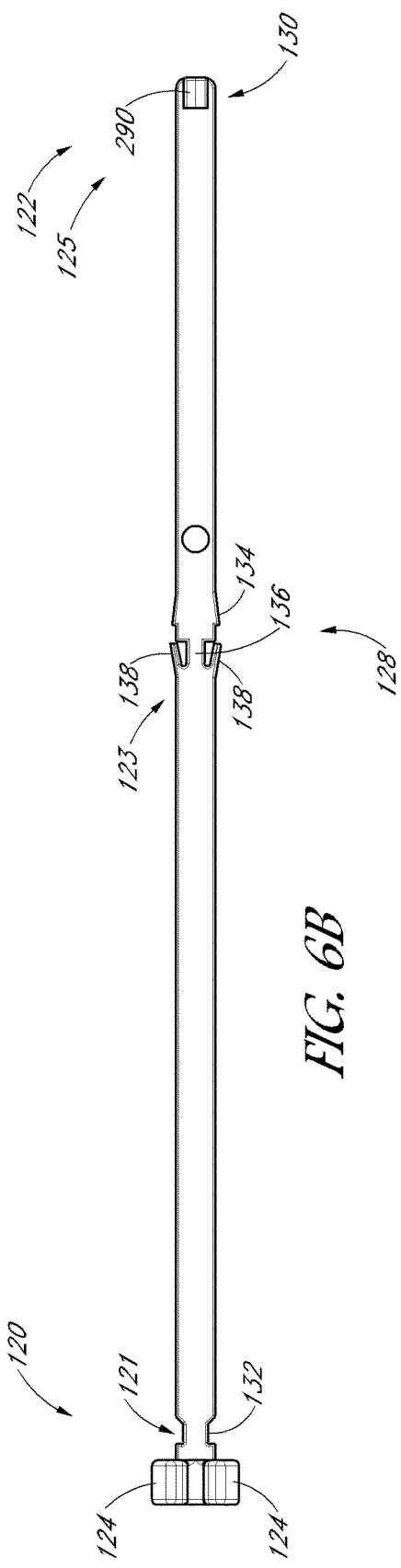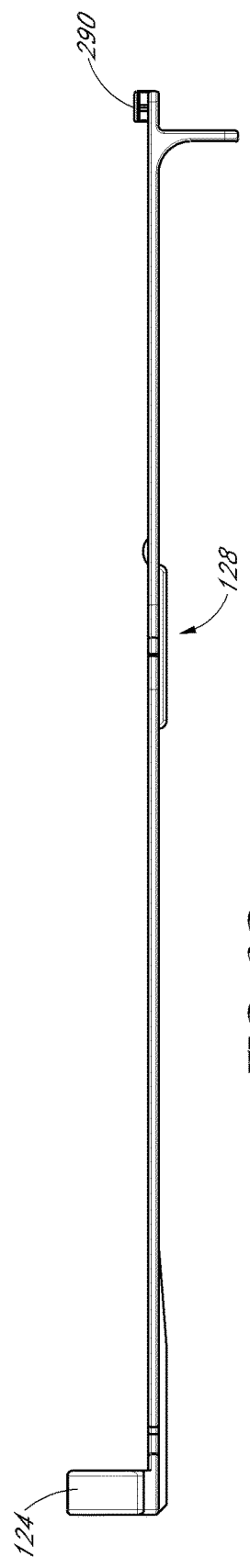
FIG. 6B
FIG. 6C

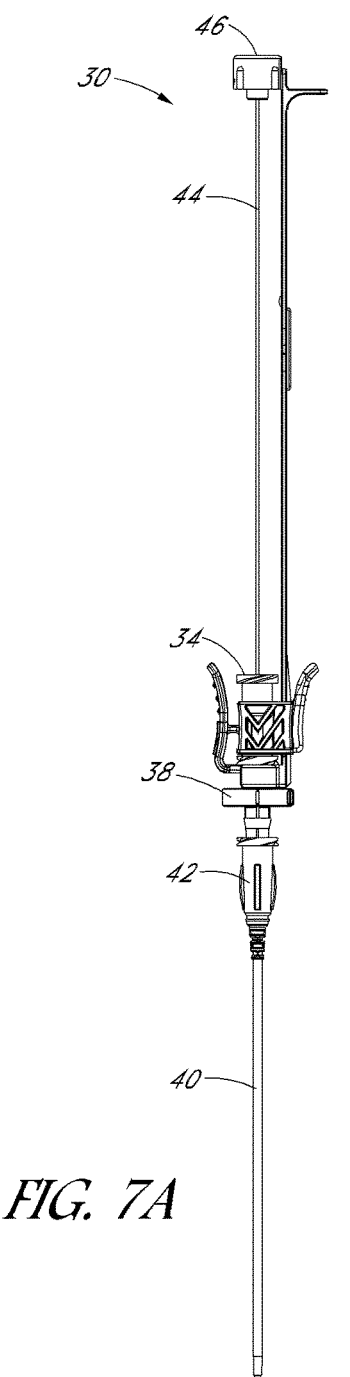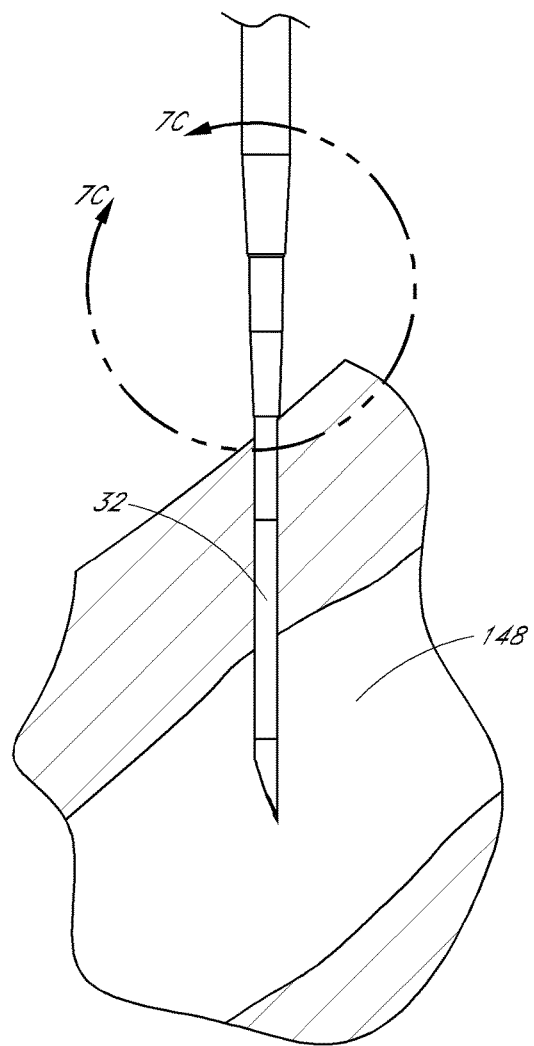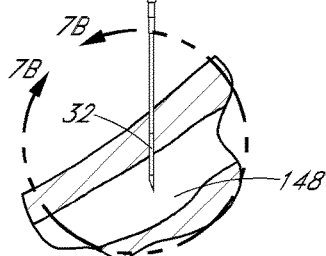
FIG. 7A
FIG. 7B

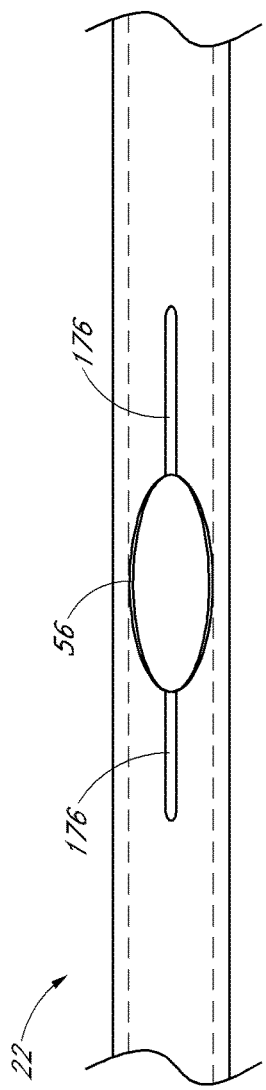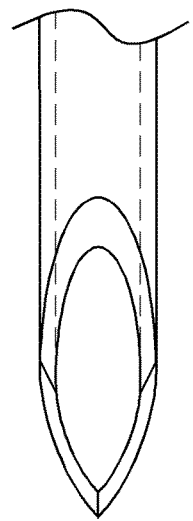
FIG. 7F
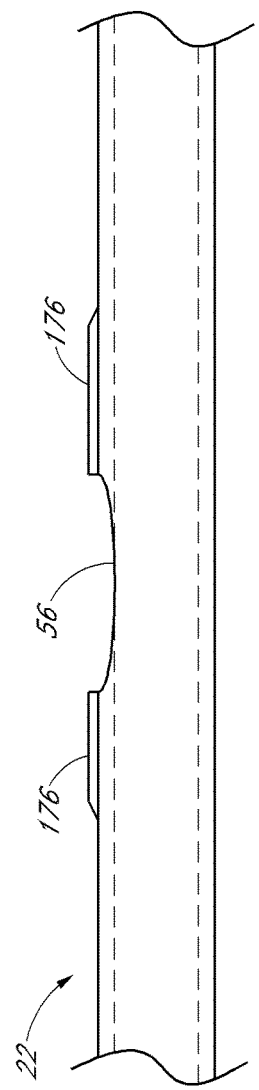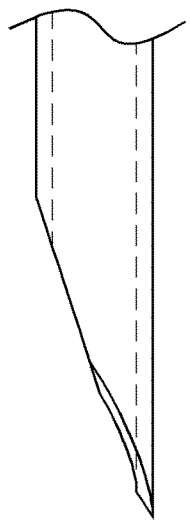
FIG. 7G

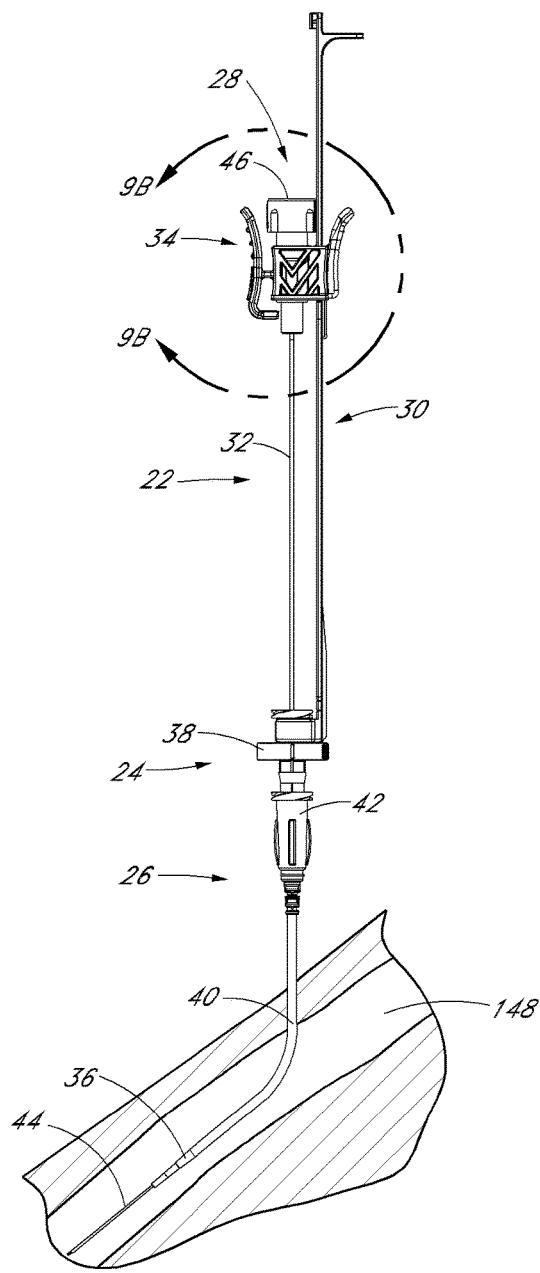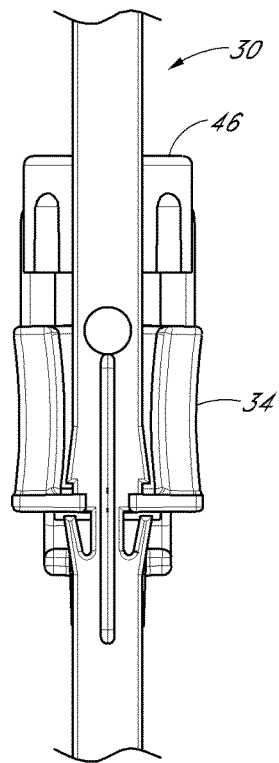
FIG. 9A
FIG. 9B

VASCULAR ACCESS DEVICE

CROSS-REFERENCE TO RELATED APPLICATIONS

This application claims priority to and the benefit of U.S. Provisional Application No. 61/799,992, filed Mar. 15, 2013, the entirety of which is hereby incorporated by reference herein and should be considered a part of this specification.

BACKGROUND

Field

The present disclosure is generally directed to access devices for introducing and/or delivering a medical article (such as, for example, a catheter, cannula, sheath, etc.) into a body space, such as, for example, an artery, vein, vessel, body cavity, or drainage site, and more specifically, to a distal tip section of such devices.

Description of the Related Art

Various medical devices, for example, catheters, cannulas, sheaths, etc., are often introduced into a patient, for example, in an artery, vein, body cavity, or drainage site, to deliver fluids to or withdraw fluids from the patient. For example, a catheter or vascular sheath can be introduced into a patient's blood vessel using the Seldinger or a modified Seldinger technique. These techniques involve inserting an access needle into the patient's blood vessel and then inserting a guidewire through the needle and into the vessel. A dilator and sheath in combination or separately are inserted over the guidewire through tissue into the vessel. The needle can be removed before or after inserting the dilator and sheath. The dilator and guidewire are then removed and discarded. The sheath can be left in the vessel, for example, to deliver medical fluids to the patient, or a catheter or other medical article can be inserted through the sheath into the vessel to a desired location.

Various access devices for performing the Seldinger or a modified Seldinger technique are known. Some access devices provide the needle, dilator, and/or sheath coaxially disposed about one another. Some such devices provide mechanisms for confirming vascular access.

SUMMARY

The access devices described herein advantageously provide improved mechanisms form confirming vascular access.

In some embodiments, an access device for placing a medical article within a body space includes a needle, a dilator coaxially disposed about the needle, and a inner member coaxially disposed between the needle and the dilator. The needle includes a fenestration near a distal end of the needle. A distal end of the dilator is positioned distal to the fenestration of the needle. A distal end of the inner member is positioned distal to the fenestration and proximal to the distal end of the dilator. A space between an outer diameter of the needle and an inner diameter of the inner member defines a blood flash channel in fluid communication with the fenestration to allow blood to flow from an interior of the needle through the fenestration to the blood flash channel when the needle punctures a blood vessel.

In some embodiments, an access device for placing a medical article within a body space includes a needle, a dilator, and a inner member. The needle includes a cylindrical body extending proximally along a needle lumen from a distal opening to a fenestration. An outer surface of the cylindrical body is disposed at a radius $r_1$ from the central longitudinal axis of the needle lumen. The dilator includes a cylindrical body extending proximally along a dilator lumen. An inside surface of the dilator is disposed at a radius $r_2$ from the central longitudinal axis of the dilator lumen, and a portion of the cylindrical body of the dilator is configured to be disposed about the needle distal to the fenestration. The inner member includes an inner portion, an outer portion, and a dimension defined therebetween. The dimension is less than $r_2-r_1$ such that the inner member can be positioned in a flash channel between the needle and the dilator.

In some embodiments, a sheath assembly includes a sheath body, a hub, and a valve including an annular member and a sealing member. The sheath body includes a generally flexible tubular structure, a proximal end, and a distal end and defines a longitudinal axis. The hub is coupled with the proximal end of the sheath body, and the sheath body and hub have aligned openings forming a passage therethrough. The annular member of the valve is disposed against a surface of the hub facing the sheath body and includes an opening therethrough. The sealing member of the valve has an engagement portion coupled with a structure of the sheath assembly disposed generally between the surface of the hub and the distal end of the sheath body. The sealing member also has a seal portion projecting into sealing engagement with the opening in the annular member in a sealing position and disposed away from the opening in the annular member in an open position.

In some embodiments, a sheath assembly includes a sheath body and hub. The sheath body includes a generally flexible tubular structure, a proximal end, and a distal end, and defines a lumen along a longitudinal axis. The hub is coupled with the proximal end of the sheath body and has a passage therethrough. The sheath assembly further includes a soft polymeric diaphragm coupled with a distal face of the hub. The diaphragm provides fluid communication between the lumen and the passage when open and has a proximal face configured to seal against a device disposed in the passage, diaphragm and lumen of the sheath assembly.

BRIEF DESCRIPTION OF THE DRAWINGS

The foregoing and other features, aspects, and advantages of the embodiments of the invention are described in detail below with reference to the drawings of various embodiments, which are intended to illustrate and not to limit the embodiments of the invention. The drawings comprise the following figures in which:

FIG. 2C is a cross-sectional view taken along the lines 2C-2C in FIG. 2A.

FIG. 2D is an enlarged plan view of a portion of the needle of FIG. 2A.

FIG. 3A is a plan view of the dilator from FIG. 1A.

FIG. 3B is a cross-sectional view taken along the lines 3B-3B in FIG. 3A.

FIG. 4G is a side cross-sectional view of the sheath of FIG. 4E taken at 4G-4G.

FIGS. 4H-4I are enlarged views of a section of the sheath of FIG. 4G showing a valve element in a closed and opened position, respectively.

FIG. 5A is a perspective view of the guidewire section from FIG. 1A and shows a guidewire hub connected to a proximal end of a guidewire.

FIG. 5B is a plan view of the guidewire section of the embodiment depicted in FIG. 5A.

FIG. 6B is a plan view of the track in FIG. 6A and shows a locking mechanism for locking the needle relative to the dilator.

FIG. 6C is a side view of the track in FIG. 6B.

FIG. 7A is a plan view of the embodiment depicted in FIG. 1A illustrating the insertion of the distal end of the access device into a patient.

FIG. 7B is an enlarged view of the embodiment depicted in FIG. 8A focusing on the area of the access device adjacent to the patient.

FIG. 7F is a plan view of a distal portion of another embodiment of a needle, with interior features in phantom.

FIG. 7G is a side view of the needle of FIG. 7F.

FIG. 9A is a side view of the embodiment depicted in FIG. 1A illustrating the dilator and sheath being advanced distally relative to the needle body from the position illustrated in FIG. 8A.

FIG. 9B is an enlarged bottom view of the embodiment depicted in FIG. 9A focusing on the area where the needle hub is locked to the track when the needle hub is in the second position.

DETAILED DESCRIPTION

Figure 1A:
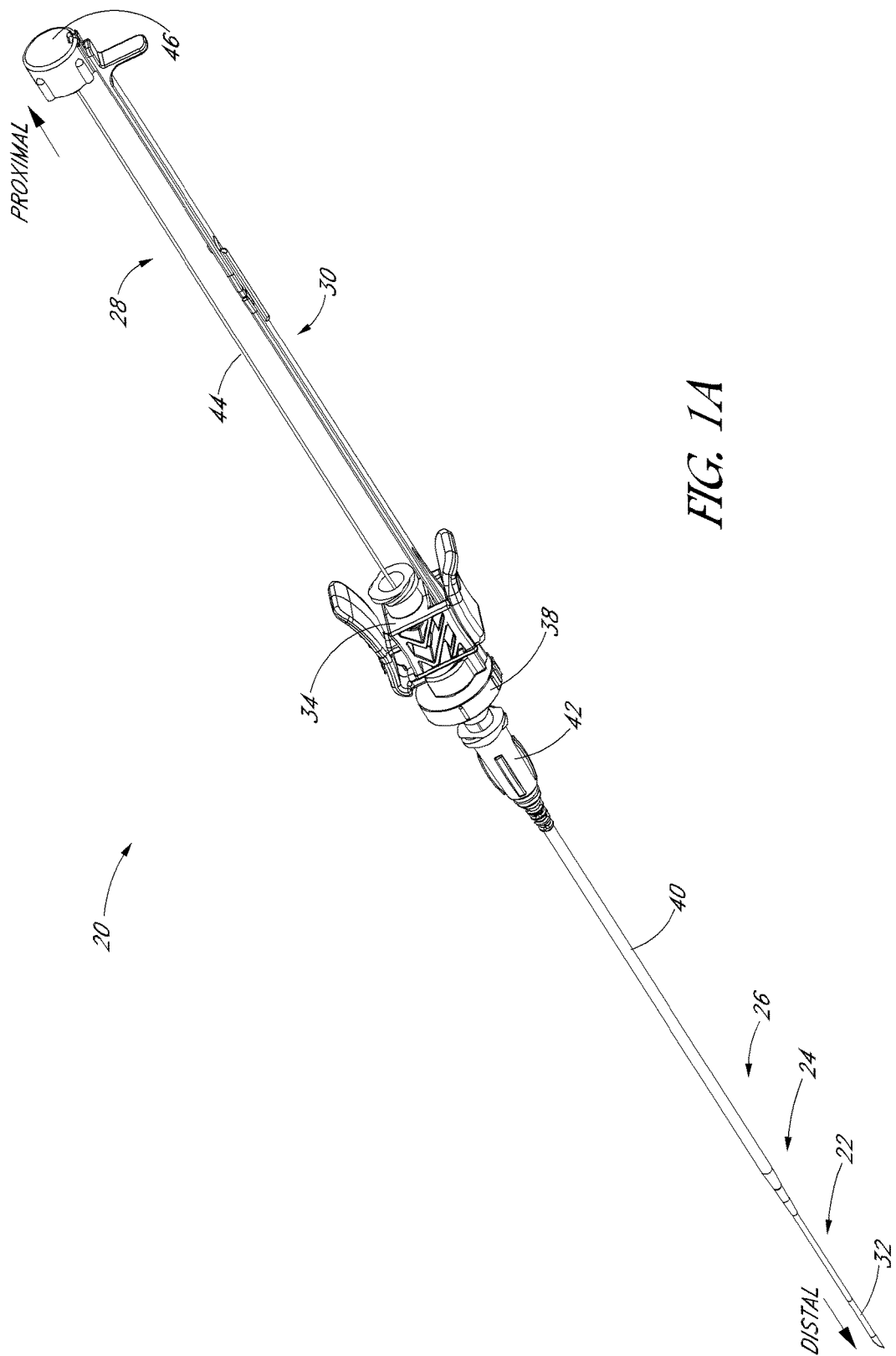
FIG. 1A is a perspective view of an embodiment of an access device having a pre-loaded guidewire coaxially aligned with a needle, a dilator, and a medical article such as a sheath.
Figure 1B:
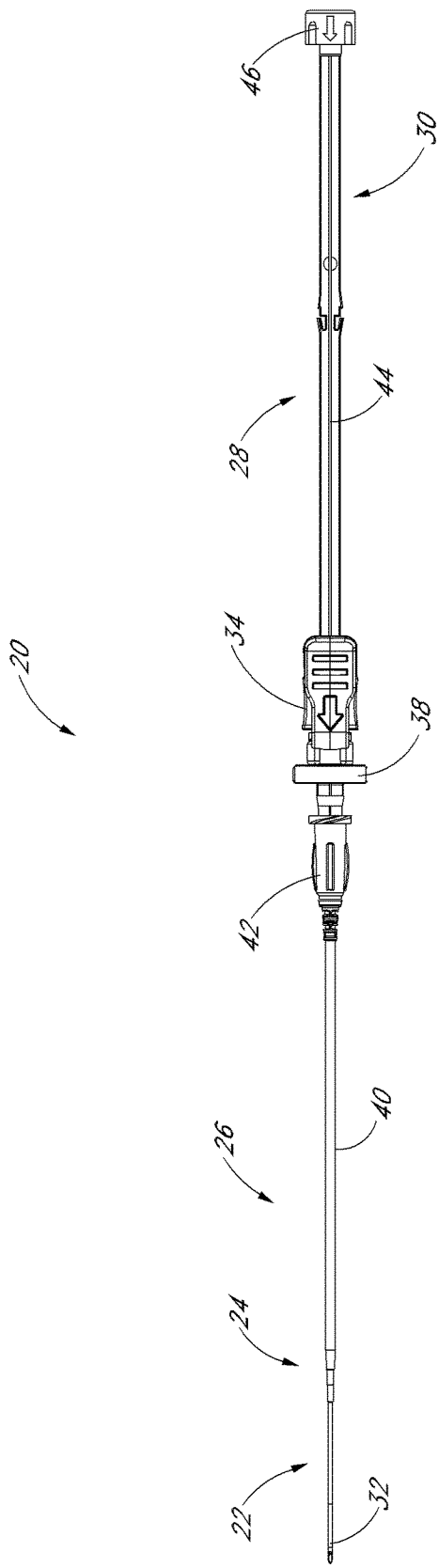
FIG. 1B is a plan view of the embodiment depicted in FIG. 1A.
Figure 2A:
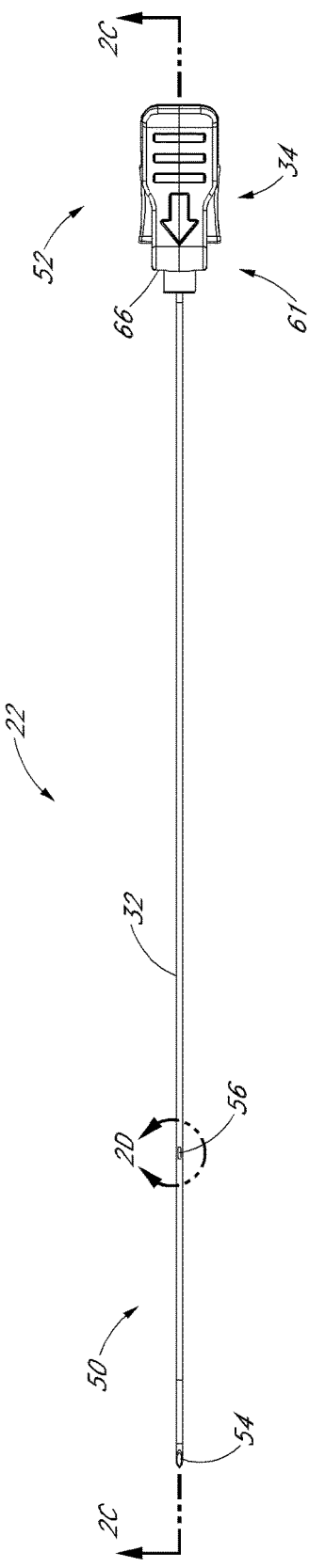
FIG. 2A is a plan view of the needle from FIG. 1A.
Figure 2B:
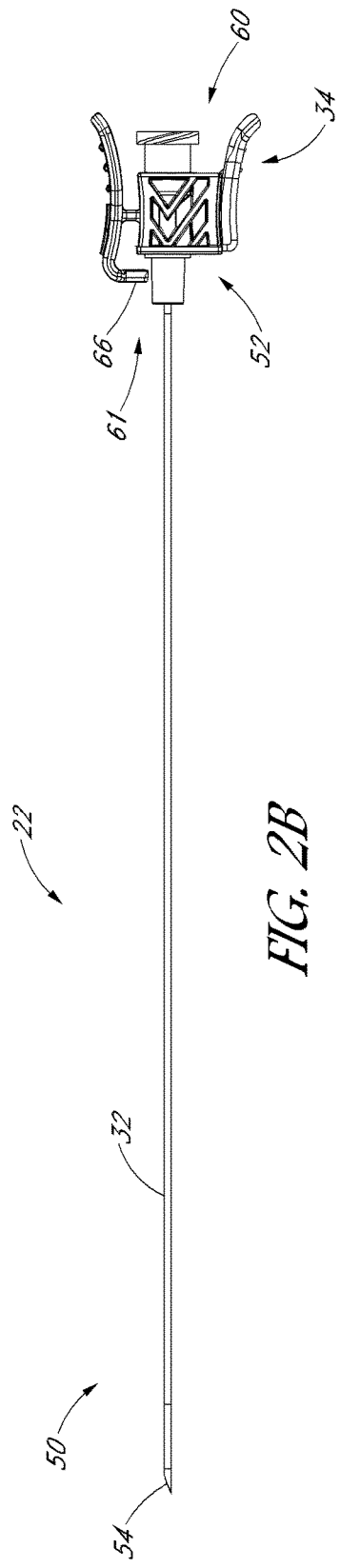
FIG. 2B is a side view of the needle from FIG. 1A.

In various circumstances a physician may wish to introduce a catheter or sheath into a space within a patient's body, for example, a blood vessel or drainage site, to introduce fluids to the space or remove fluids from the space. Various access devices are known in the art. Examples of an improved access device are described in International Application No. PCT/US2012/051495, entitled "ACCESS DEVICE WITH VALVE," filed Aug. 17, 2012, the entire contents of which is incorporated by reference herein and forms part of this specification. FIGS. 1A and 1B illustrate an access device 20 that can be used, for example, in performing the Seldinger or a modified Seldinger technique to introduce a catheter or sheath to a patient's blood vessel. While the access device is described herein in the context of vascular access, the access device also can be used to access and place a medical article (e.g., catheter or sheath) into other locations within a patient's body (e.g., a drainage site) and for other purposes (e.g., for draining an abscess).

The present embodiment of the access device is disclosed in the context of placing an exemplary single-piece, tubular medical article into a body space within a patient. Once placed, the tubular article can then be used to receive other medical articles (e.g., catheters, guidewires, etc.) to provide access into the body space and/or be used to provide a passage way for introducing fluids into the body space or removing (e.g., draining) fluids from the body space. In the illustrated embodiment, the tubular medical article is a sheath or catheter that is configured primarily to provide a fluid passage into a vein. The principles of the present invention, however, are not limited to the placement of single piece sheaths or catheters, or to the subsequent insertion of a medical article via the sheath or catheter. Instead, it will be understood in light of the present disclosure that the access device disclosed herein also can be successfully utilized in connection with placing one or more other types of medical articles, including other types of sheaths, fluid drainage and delivery tubes, and single or multi-lumen catheters directly in the patient or indirectly via another medical article.

For example, but without limitation, the access devices disclosed herein can also be configured to directly or indirectly place central venous catheters, peripherally inserted central catheters, hemodialysis catheters, surgical drainage tubes, tear-away sheaths, multi-piece sheaths, PICC lines, IV lines, scopes, as well as electrical conduit for wires or cables connected to external or implanted electronic devices or sensors. As explained above, the medical articles listed above may be directly placed in the patient via the dilator, needle, and guidewire of the access device or subsequently placed within the patient via a medical article that was placed within the patient via the dilator, needle, and guidewire of the access device.

Further, the embodiments disclosed herein are not limited to co-axial insertion of a single medical article. For example, two catheters may be inserted in the patient via an inserted sheath or a second catheter may be inserted in the patient via an inserted first catheter. Further, in addition to providing a conduit into the vessel or other body space, the medical article inserted via the dilator, needle, and guidewire can form a lumen that is in addition to the lumen(s) of the subsequently inserted medical article. One skilled in the art can also find additional applications for the devices and systems disclosed herein. Thus, the illustration and description of the access device in connection with a sheath (e.g., for micro puncture applications) is merely exemplary of one possible application of the access device.

With reference to FIGS. 1A and 1B, an example embodiment of an access device 20 includes a needle 22, a dilator 24, and a tubular sheath 26. In the illustrated embodiment, the access device 20 also includes a guidewire 28 and guidewire track 30. The dilator 24 can be coaxially disposed about the needle 22, and the sheath 26 can be coaxially disposed about the dilator 24. The access device 20 can be configured to allow for telescoping movement among the needle 22, dilator 24, and sheath 26.

With reference to FIGS. 2A-2D, the needle 22 includes a needle body 32 and needle hub 34. The needle hub 34 is disposed on a proximal end of the needle body 32 at a proximal portion 52 of the needle 22. The needle hub 34 can include a locking structure 66 at a distal portion 61 of the needle hub 34 to allow the physician or healthcare provider to lock the needle hub 34 to a medical article such as a dilator hub 38 as described in greater detail herein. The needle hub 34 can also include a locking structure at a proximal portion 60 of the needle hub 34 to allow the physician or healthcare provide to secure (e.g., releasably secure) another medical article to the needle hub 34. The needle body 32 terminates at a distal end near a distal portion 50 of the needle 22. The distal end of the needle body 32 can have a bevel tip 54.

The needle body 32 has a sufficiently long length to access a targeted subcutaneous body space and has a sufficient gauge size to withstand the insertion forces when accessing the body space without causing undue trauma. For many applications, the needle body can have a length between 3-20 cm, and more preferably between 3-10 cm. For example, to access a body space (e.g., a vessel) in the thorax of an adult human, the needle body 32 preferably has a length of 7 cm or greater, and more preferably has a length of 9 cm or greater, and most preferably has a length of 9 to 10 cm. The size of the needle preferably is 18 gauge or smaller, and more preferably between 18-28 gauge, and most preferably between 18-26 gauge for micro-puncture applications (e.g., peripheral IVs). For applications with a neonate, the length and gauge of the needle body 32 should be significantly shorter and smaller, for example preferably between 3-4 cm and between 26-28 gauge. In some embodiments, the needle 22 includes an echogenic portion that can be used in combination with ultrasound to help position the needle in the desired location.

In some embodiments, the needle body 32 includes at least one fenestration or opening 56 near a distal end of the needle body 32. The fenestration 56 extends, or provides a path, through the wall or side of the needle body 32. The fenestration 56 can allow for a fluid, such as blood, to flow into a space between a portion of the needle body 32 and a portion of the dilator 24 during use of the access device 20, creating a "blood flash." During blood flash, blood is observed flowing between the needle 22 and dilator 24 to indicate to the physician or healthcare provider that the tip 54 of the needle body 32 has punctured a blood vessel. The fenestration 56 can have a variety of shapes and orientations on the needle body 32. For example, the fenestration 56 illustrated in FIG. 2D has an oblong shape. However, the shape of the side opening 56 is not limited to the illustrated embodiment and may be round, oblong, square, or another shape.

With reference to FIGS. 3A-3B, the dilator 24 can include a dilator body 36 and dilator hub 38. The dilator hub 38 can include a first locking structure 78 to engage the needle hub 34 and a second locking structure 80 to engage with a sheath hub 42, described in greater detail herein. For embodiments of the access device 20 having a fenestration 56 in the needle 22 to allow for blood flash, optical properties, such as the color, of the needle 22 and/or the dilator 24 can be selected to enhance the contrast between the blood or other fluid and the needle 22 and/or dilator 24. To increase the visibility of the fluid as the fluid flows between the needle 22 and the dilator 24, the dilator 24 can be manufactured from a clear or at least somewhat transparent material with the needle 22 having a color that contrasts with the color of the fluid. For example, the needle 22 can have a white or silver color to enhance its contrast with red blood.

Figure 4A:
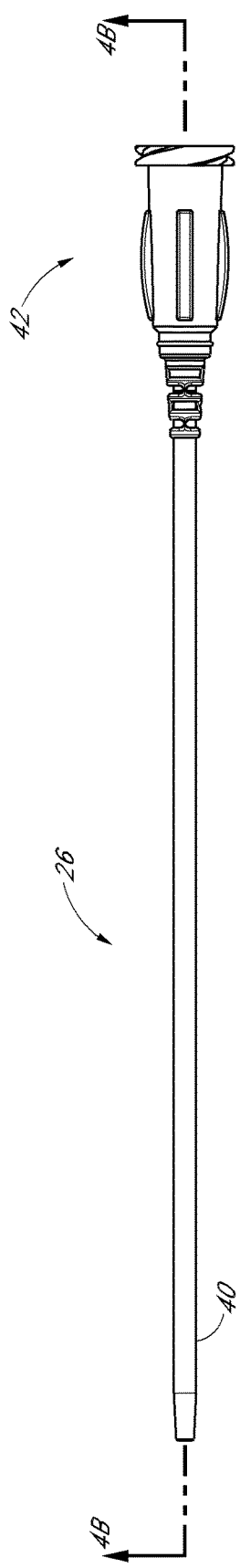
FIG. 4A is a plan view of the sheath from FIG. 1A and shows a sheath hub connected to a proximal end of a sheath.
Figure 4B:
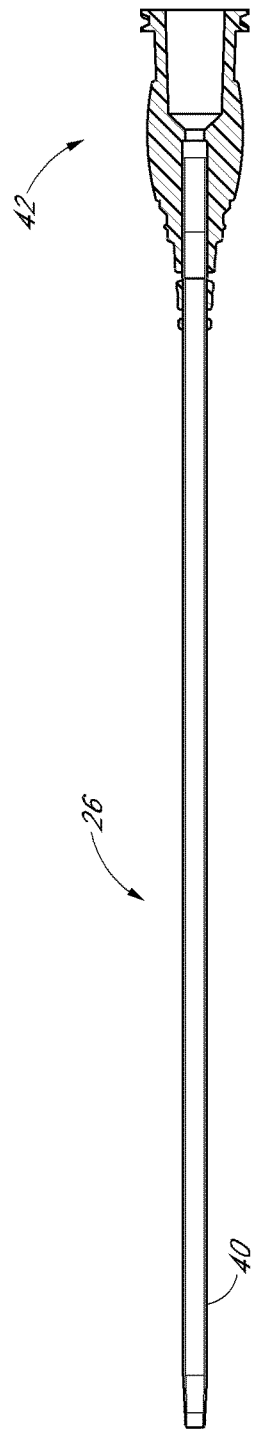
FIG. 4B is a cross-sectional view of the sheath from FIG. 4A taken along the lines 4B-4B in FIG. 4A.

As shown in FIGS. 4A-4B, the sheath 26 can include a sheath body 40 and sheath hub 42. The sheath hub 42 can include a locking structure 94 configured to engage, for example, the second locking structure 80 of the dilator hub 38. The sheath body 40 may be a single piece sheath through which a catheter or other medical article (e.g., a guidewire) is inserted into the vessel. In such an embodiment, the sheath body 40 forms a conduit for insertion of the catheter or other medical article (e.g., a guidewire). In addition to providing a conduit, the sheath or a portion of the sheath can form a lumen that is in addition to the lumen(s) of the catheter. For example, an equivalent to a triple lumen catheter can be formed by inserting a dual lumen catheter through the sheath body 40 with the sheath body 40 itself forming a third lumen. The sheath body 40 can be manufactured from a clear or at least somewhat transparent material to allow the physician or healthcare provider to see blood flowing between the needle body 32 and dilator 24 through the sheath body 40.

Figure 4C:
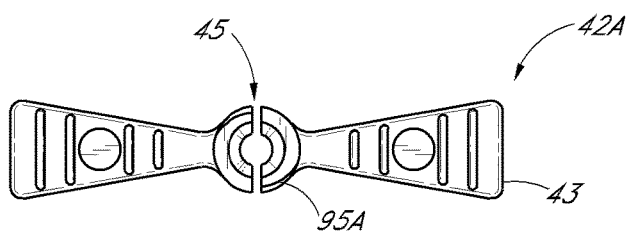
FIG. 4C is a proximal end view of another embodiment of a sheath.
Figure 4D:
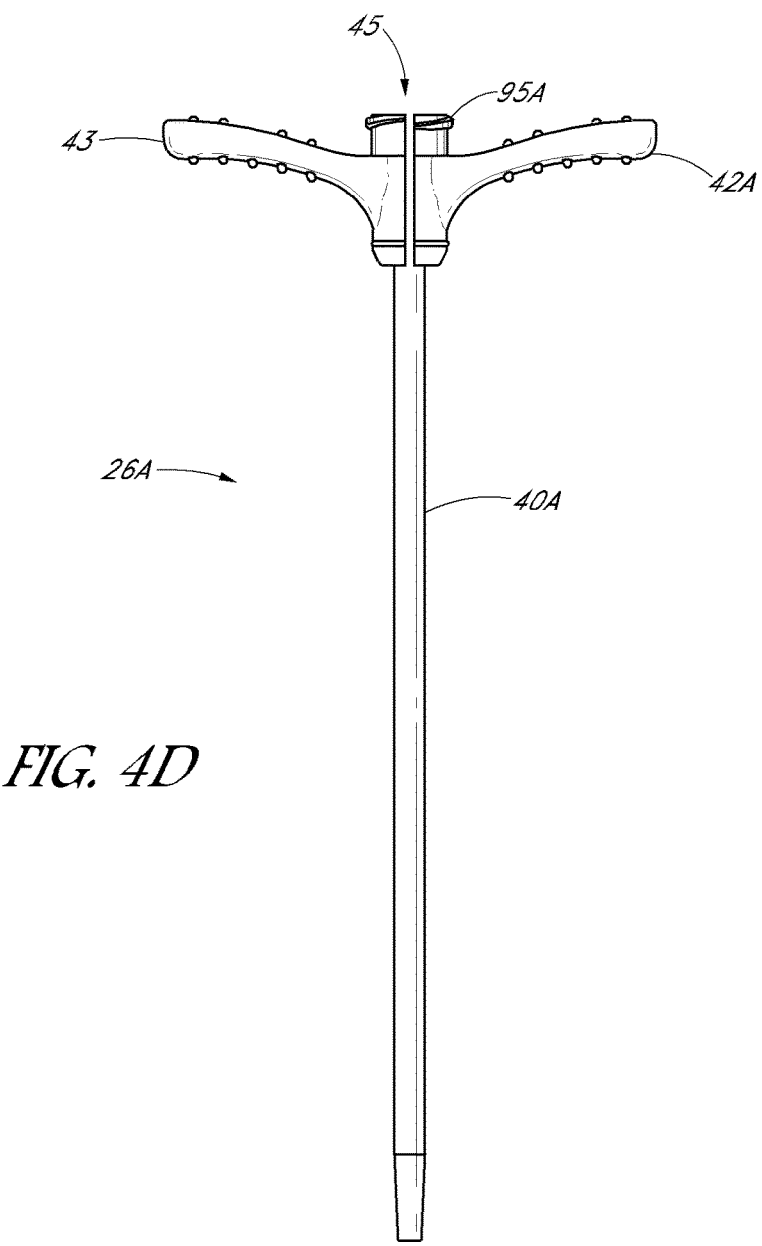
FIG. 4D is a plan view of the sheath of FIG. 4C.
Figure 4E:
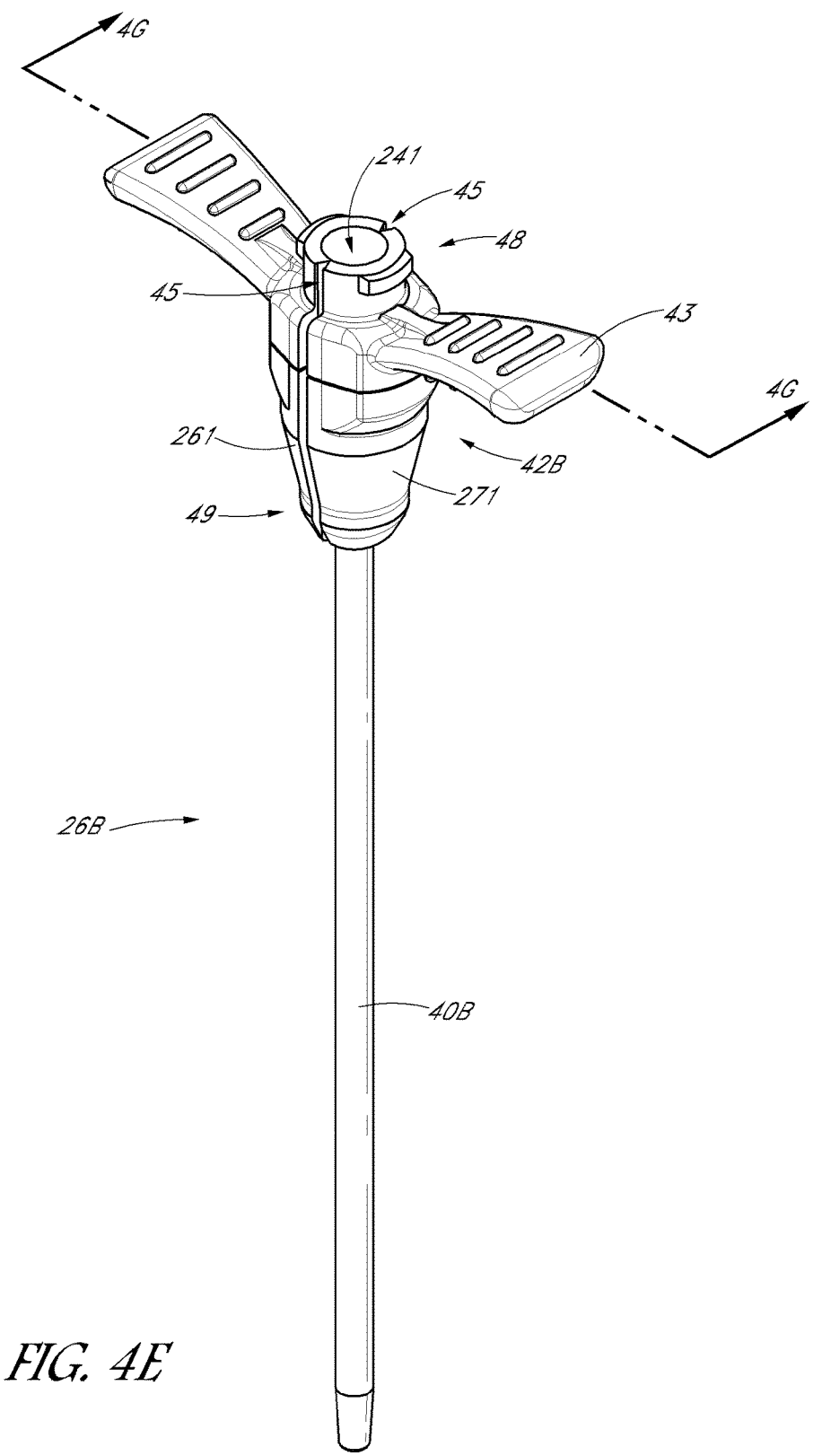
FIGS. 4E and 4F are a side isometric view and an exploded side isometric view, respectively, of an embodiment of a sheath.

In some embodiments, for example as shown in FIGS. 4C and 4D, the sheath can be a splittable sheath 26A. For example, it may be advantageous to remove a portion of or the entire sheath body 40A depending on the type of catheter or medical article that is to be inserted into the vessel after employing the access device 20. For example, after the catheter or other medical article is inserted into the vessel, a portion of the sheath body 40A can be separated or peeled-away and removed to reduce clutter at the access site. A peel-away sheath can include perforations, serrations, skives, or other structures, or include other materials (e.g., PTFE with bismuth) to allow the physician or healthcare provider to remove easily a portion or the entire sheath body 40A.

In some such embodiments, the sheath hub 42A may comprise radially extending wings, handle structures, or tabs 43 to allow for easy release and removal of the sheath body 40 from other parts of the access device 20. Tabs 43 can have any of a number of different shapes and/or surface features to facilitate them being gripped, and are not limited to the substantially T-shape shown. Tabs 43 are separable, to allow the splittable sheath 40A to separate along one or more split lines, such as a predetermined split or separation line 45. The split line 45 can extend through either or both the sheath hub 42A and the sheath body 40A. The split line(s) can extend generally parallel to one or more longitudinal axes defined by the sheath body 40A and/or sheath hub 42A, but in some embodiments, the split line(s) can extend substantially non-parallel. As illustrated, splitting the sheath 26A along the split line 45 can separate the sheath 26A into two or more symmetrical or asymmetrical portions (e.g., halves). The sheath 26A can include similar additional features described herein for sheath 26. In some embodiments, sheath 26A can include similar features that are also configured to be separable into one or more portions along split line 45. For example, sheath 26A can have a separable lip 95A, allowing engagement of sheath 26A with other elements described above, such as the dilator 24, while allowing separation along split line 45. Additional embodiments of a splittable sheath body and/or hub that can be employed with sheath 26A are shown and described, for example, in FIGS. 23A-23B, and the corresponding supporting text (e.g., paragraphs [0223]-[0227]), of PCT International Patent Application No. PCT/US2010/034609, filed May 12, 2010, hereby incorporated by reference in its entirety herein. In some applications, the wings are sized to provide the healthcare provider with leverage for breaking apart the sheath hub 42. The sheath hub 42 and/or the sheath body 40 may comprise two or more portions (e.g. halves) connected by a thin (e.g., frangible) membrane. The membrane can be sized to hold the two or more portions of the sheath hub 42 and/or sheath body 40 together until the healthcare provider decides to remove the sheath hub 42 and/or sheath body 40 from the access device. The healthcare provider manipulates the wings to break the membrane and sever one or more portions of the sheath hub 42 into separate or partially separated pieces.

FIGS. 4E-4I illustrate another embodiment of a sheath that can be used with the dilators, needles, guidewires, and other elements described herein in a similar manner to the previously described sheaths is sheath 26B. Sheath 26B can include a sheath body 40B and a sheath hub 42B, with an inner cavity 241 extending through or along a portion of sheath body 40B and/or sheath hub 42B (e.g., along one or more longitudinal axes thereof). Sheath hub 42B can extend from a proximal end of sheath body 40B. Sheath body 40B and/or sheath hub 42B can be optionally splittable along one or more split lines 45. In some embodiments, sheath body 40B and/or sheath hub 42B can be splittable along two or more split lines 45, to form two or more separable sections or halves, such as sheath hub sections 261 and 271. The embodiments of sheath 26B, including body 40B and hub 42B, can be generally similar to the embodiments of sheaths, sheath bodies, and/or sheath hubs discussed elsewhere herein.

With reference to FIGS. 4F-4I, sheath 26B can include a valve element 240 configured to substantially seal a portion of inner cavity 241. Valve element 240 can include a resilient plate 242 supporting a sealing element 243. The resilient plate 242 can be supported by a portion of the sheath body 40B and/or hub 26B such that a portion (e.g., a sealing portion 264) of the resilient plate 242 can extend (e.g., radially inwardly) into and substantially seal the inner cavity 241. Valve element 240 can be positioned between a proximal portion 244 of inner cavity 241 and a distal portion 245 of inner cavity 241, such that proximal portion 244 and distal portion 245 can be substantially sealed with respect to each other. Portions 244, 245 can comprise any of a variety of sizes and shapes, and are shown with an approximately circular cross-sectional shape for illustrative purposes only. In the depicted embodiment, proximal portion 244 of inner cavity 241 comprises at least a region having a cross-sectional area that is less than distal portion 245, to facilitate sealing of valve 240 against portion 244, while allowing valve 240 to flex and move distally into distal portion 241, as described further herein. In this arrangement, the valve 240 can be configured to substantially inhibit flow through the inner cavity 241 in a proximal direction, while not substantially inhibiting the passage of articles such as a dilator or needle through the cavity.

Valve element 240 can be adapted to flex or move between a closed, or substantially sealed position (for example, as shown in FIGS. 4G and 4H), and an open, or substantially unsealed position (for example, as shown in FIG. 4I), through flexation or flexing of resilient plate 242. Valve element 240 can move between an open and closed position through passage of a fluid (or gas), a device, or through an operation by a user (for example, using an external lever or other device attached to resilient plate 242). In the closed position, a sealing surface 266 on a proximal surface of the sealing element 243 can contact or otherwise engage with a corresponding sealing surface 267 on a distal surface of at least one of the splittable sheath body and hub 40B, 42B. The interaction of the sealing surfaces 266 and 267 can inhibit passage through the cavity 241 in the proximal direction. Notably, pressure against the valve element 240 in a proximal direction can press the sealing surfaces 266 and 267 further together. In some embodiments, this mechanism can be sufficiently resilient to withstand pressures associated with human blood vessels to prevent a loss of blood through the valve. In some embodiments, the sealing element 243 includes a raised portion, such as substantially dome-shaped portion 278. The dome-shaped portion 278 can prevent or reduce the likelihood of contact between the sealing surface 266 and a device 263, when the device 263 is extended through cavity 241. For example, if sheath 26B is stored with a device extended through the cavity 241, for example, a dilator 24 as described herein, if the device sets or sticks to another portion of the sheath 26B, it will do so to the raised portion 278, and not to a portion of the sealing surface 266. As such, the raised portion 278 can prevent damage to the sealing surface 266 of the sealing element 243 by extended forceful contact with the device 263, and thus extend the sealing capability and life of the valve element 240.

In some embodiments, the resilient plate 242 is configured such that the sealing surface 266 of the sealing element 243 is biased or preloaded against sealing surface 267 of the splittable sheath body and/or hub such that valve 240 is preloaded in the closed position. This biasing can enhance the above-described inhibition of passage of matter in the proximal direction. Additionally, the biasing can help the valve element 240 inhibit passage of matter such as the flow of fluid or gas (e.g., blood flash, or air) or passage of a device in a distal direction (e.g., longitudinally) within cavity 241. For example, the bias towards the closed position can be strong enough to resist a force (or cracking pressure) in the distal direction to open the valve element 240. In some embodiments, the preload or bias of valve element 240 can be sufficient to prevent gas from being drawn distally through cavity 241, and into a patient due to, for example, negative pressure created by a human during a normal pulse. Notably, drawing gas into a blood vessel can cause serious health effects such as an embolism.

Resilient plate 242 can comprise any of a variety of materials with sufficient rigidity to support sealing element 243 and substantially seal inner cavity 241, and with sufficient flexibility to allow valve element 240 to flex or move between the open and closed positions described herein. Resilient plate 242 can comprise a bio-compatible metal or plastic, or various composites or combinations thereof. Preferably, resilient plate 242 can comprise a material with reduced susceptibility to cold-setting, such that a needle, dilator, catheter, or other medical article can be extended through cavity 241, with valve element 240 in an open position, as described above, and packaged together for a period of time within the sheath 26B, without compromising the valve features (e.g., its flexibility and ability to seal cavity 241 when in a closed position). In some embodiments, resilient plate 242 can comprise, Nickel, Titanium, and/or steel (e.g., stainless steel, spring steel, etc.), or various alloys or combinations thereof. In some embodiments, resilient plate 242 comprises NiTi (Nitinol), or NiTi SE. In some embodiments, the resilient plate 242 can comprise a shape-memory alloy to facilitate its movement between an opened and closed position and to prevent cold-setting for extended periods of time such as 2 years.

Sealing element 243 can comprise any of a variety of materials that can substantially seal inner cavity 241 when in contact with or biased against sealing surface 267. In some embodiments, sealing element 243 can comprise metal, plastic, rubber, or other suitable biocompatible materials such as polyisoprene, silicone, polyurethane, or other elastic polymers. In some embodiments, the Shore A hardness of sealing element 243 can be within a range of approximately 5 to 90, or in some embodiments, 10 to 70, or in some embodiments, approximately 15 to 50, or in some embodiments, approximately 30. In some embodiments, the sealing element 243 can be coated or include other surface treatments, such as a siliconized surface to facilitate low-friction sliding of various elements along its surface (such as device 263). Even further, in some embodiments the resilient plate 242 and the sealing element 243 can be formed of the same material, such that the valve element 240 can optionally be a single unitary piece.

Resilient plate 242 and/or element 243 can be formed in a number of different ways, such as molding (e.g., injection), stamping and the like, and can be formed separately or integrally. Resilient plate 242 and sealing element 243 can be attached to each other in a variety of ways, such as with adhesive, bonding (e.g., ultrasonic, thermal, etc.), fasteners, overmolding, and the like. A primer or non-stick coating or surface treatment can be applied to plate 242 and/or sealing element 243 to facilitate their attachment to each other during the manufacturing thereof. In some embodiments, a plurality of plates 242 and/or elements 243 can be formed in a single molding or stamping step, with severable tabs to allow the plates 242 and/or elements 243 to be used individually. With respect to the bending properties of the resilient plate 242, described above, in some embodiments the resilient plate 242 can be pretreated to have certain mechanical characteristics prior to its combination with the sealing element 243.

The valve element 240, as depicted by way of the resilient plate 242, can attach to the sheath 26B by a variety of means.

In some embodiments it can be glued or bonded to the sheath 26B. In other embodiments, the resilient plate 242 can attach to the sheath 26B by molding or overmoulding. In further embodiments, the resilient plate 242 can be molded integrally with the sheath 26B (or a portion thereof such as the sheath hub half). When formed integrally, it may be desirable to give the hub 42B or body 40B a substantially greater thickness than the resilient plate 242, such that the hub or body maintains a higher rigidity. In other embodiments the resilient plate 242 can attach to the sheath 26B by a mechanical compression, such as where the sheath hub 42B or body 40B includes a groove that receives the plate, and allows it to be press-fit into position.

Figure 4F:
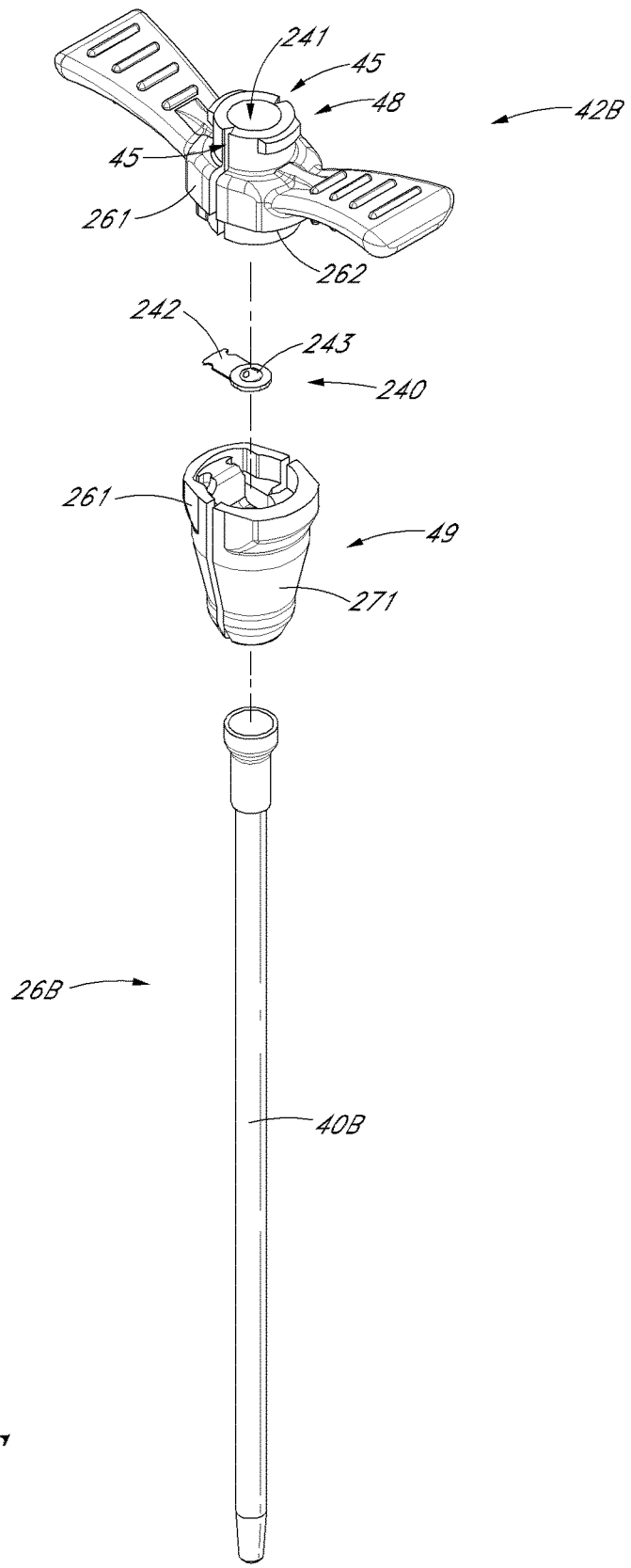

Resilient plate 242 can be attached to various portions of sheath hub 42B and/or body 40B. In some embodiments, the sheath hub 42B and/or body 40B can comprise two or more separate pieces that are positioned and attached with respect to each other such that a portion of resilient plate 242 is clamped between a portion of sheath hub 42B and/or body 40B. As best shown in FIGS. 4F, 4H, and 4I, sheath hub 42B can comprise a proximal portion 48 and a distal portion 49, configured to engage with each other such that the valve element 240, by way of a mounting portion 265 of the resilient plate 242, can be supported or clamped therebetween within a groove or gap 274 (as shown in FIG. 4I). Portions 48, 49 can comprise any of the materials described herein generally for sheath 26B and other components thereof, such as sheath hub 42B and sheath body 40B. In one embodiment, portion 48 comprises ABS plastic. In one embodiment, portion 49 comprises a K resin. Portions 48, 49 can engage with each other using any of a variety of attachment means and methods known or described herein, such as bonding, adhesive (e.g., solvents), and the like.

The valve element 240, and resilient plate 242, can be attached to one or more sections of sheath hub 42B and/or body 40B that separate along line(s) 45. Preferably, resilient plate 242 is attached to only one separable section of sheath 26B, such as sheath hub section 261, to facilitate the separation of valve 240 from sheath hub section 271 during the splitting of sheath 26B. Additionally, plate 242 can be attached to only one separable section of sheath 26B to facilitate the flexing and movement of resilient plate 242 and sealing element 243 within inner cavity 241. In other embodiments, where the valve element 240 is attached to multiple separable portions of the sheath hub 42B and/or body 40B, the valve element 240 can also be separable by similar structures.

Figure 4J:
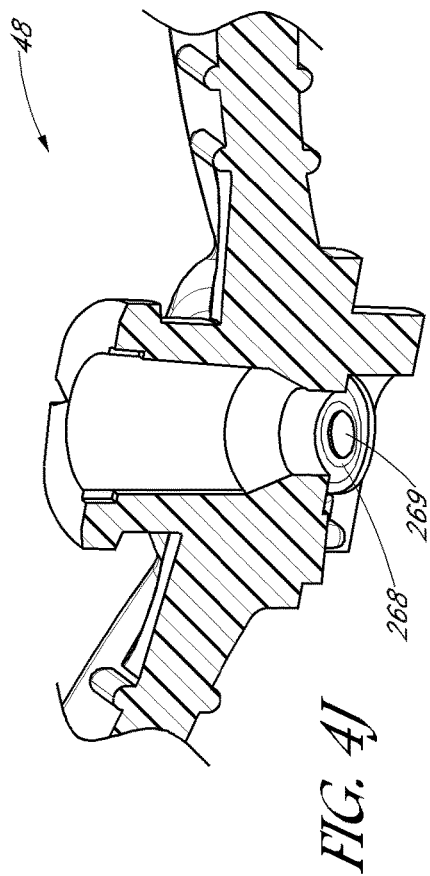
FIGS. 4J-4L are enlarged views of a section of an embodiment of a valve element.
Figure 4L:
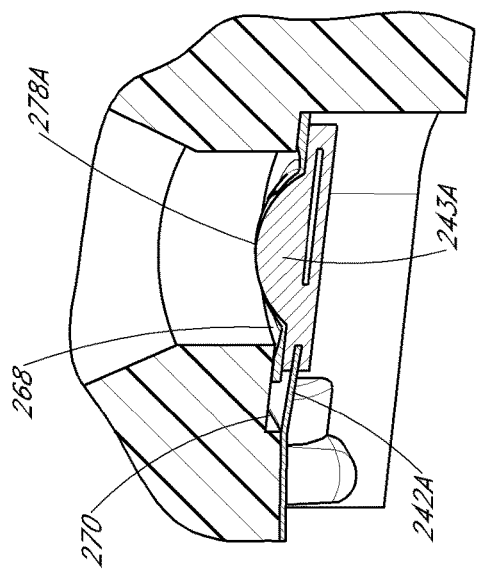
Figure 4K:
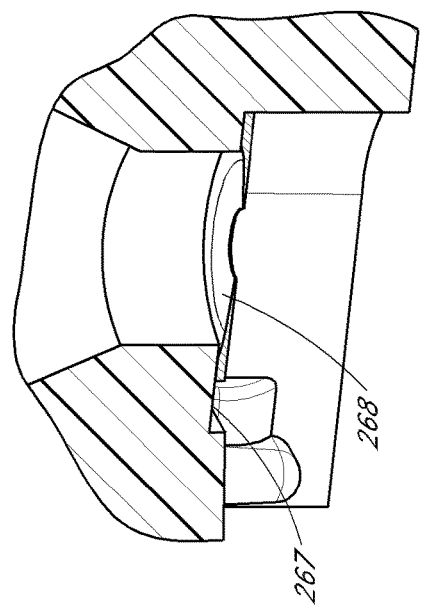
Figure 6A:
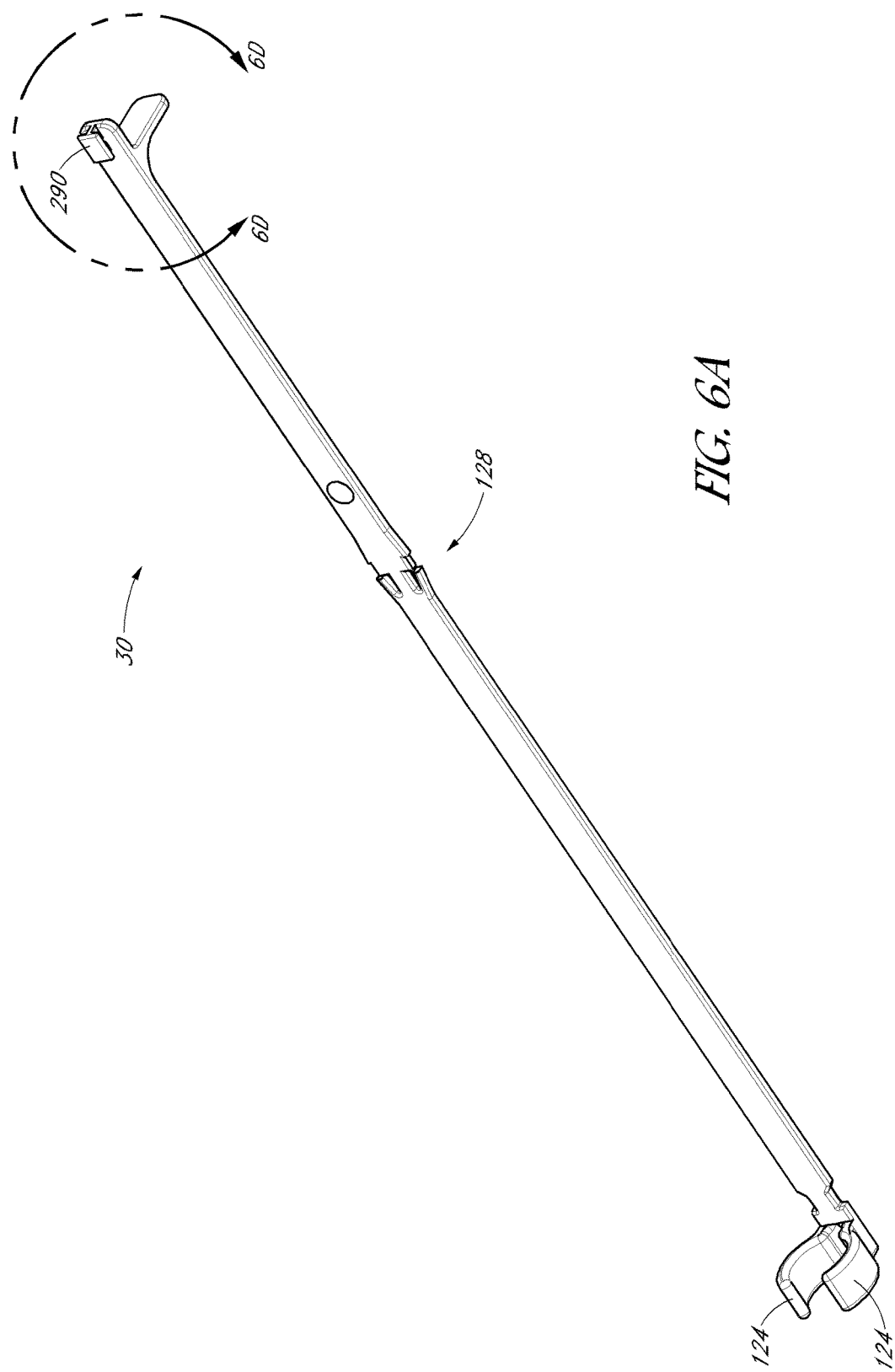
FIG. 6A is a perspective view of a track from FIG. 1A.
Figure 6D:
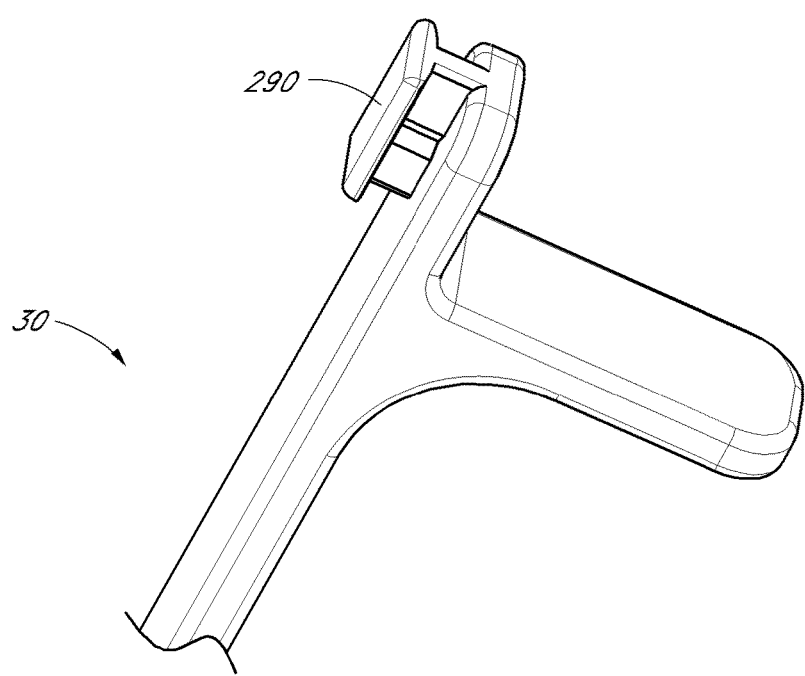
FIG. 6D an enlarged perspective view of the locking mechanism from FIG. 6B.

FIGS. 4J-4L show further embodiments that include an annular member 268 and a resilient plate 242A and sealing element 243A. The plate 242A and sealing element 243A can be similar to the resilient plate 242 and sealing element 243 shown in FIGS. 4F-4I and described herein. The annular member 268 can function like an O-ring in some respects. As shown, the annular member 268 includes a central bore 269 configured to receive the domed-shaped portion 278A of the sealing element 243A when the valve is in a closed position. A top surface of the annular member 268 tapers so that the annular member is thinner proximate the bore 269 than at a location outward of the bore 269, e.g., at the outer edge. The taper can be downwardly from an upper surface in some embodiments. A bottom surface of the annular member 268 can be substantially straight or flat. The annular member 268 is placed against the sealing surface 267 so that in a closed position, the sealing element 243A seals against the annular member 268 rather than the sealing surface 267. The annular member 268 can be made of a relatively soft material, and can be thin enough to tear during splitting of the sheath 26B. The annular member 268 can advantageously compensate for possible molding imperfections and/or misalignment in the manufacture and assembly of the sheath hub, for example, due to being constructed from a relatively soft and compliant material. The annular member 268 also advantageously reduces the size of the aperture to be sealed by the sealing element 243A compared to the sealing surface 267, which can produce a greater vacuum hold to bias the sealing element 243A in a closed position with the same spring pre-loading force of the resilient plate 242A. Additionally, the annular member 268 can act as a seal around a device introduced into the patient through the sheath 26B to maintain a seal when the valve 240 is in an open position to accommodate the device. The annular member 268 can therefore act as a seal independent of the sealing element 243A. In some embodiments, the annular member 268 can stretch to accommodate and/or conform to various devices that can be introduced through the sheath 26B.

In some embodiments, the sealing element 243A can be made of a relatively hard material, for example, polyurethane or polycarbonate. Inclusion of a relatively soft annular member 268 can advantageously allow the sealing element 243A to be made of a relatively hard material because the more compliant annular member 268 can compensate for molding imperfections, misalignment, and the like for which a relatively hard sealing element 243A may not be able to compensate as effectively. The relatively hard material can advantageously reduce possible damage to the resilient plate 242A. Additionally, with a sealing element 243A made of a relatively softer material, for example, silicone, the resilient plate 242A may bend to some extent anywhere along its length when the valve is opened. With a sealing element 243A made of a relatively harder material, bending of the resilient plate 242A may be relatively more limited to a pivot axis 270, which can reduce possible damage and/or wear to the resilient plate 242A. The relatively hard material can also better resist tearing and/or other wear. Such tearing or wear can adversely affect the effectiveness of the seal or expose sharp portions of the resilient plate 242A, which can cut or otherwise damage other instruments, for example a dilator 24 as described herein, inserted into and/or removed from the sheath 26B through the valve 240.

As shown in FIGS. 5A-5B, the guidewire 28 can include a guidewire body 44 and guidewire hub 46. The guidewire hub 46 can have a structure corresponding to a coupling section 290 on the guidewire track 30, shown in FIGS. 6A-6D, to releasably connect the hub 46 to the track 30. The guidewire track 30 can also include a distal locking member 124 to connect the track 30 to the dilator hub 38, and a locking mechanism 128 for the needle hub 34.

The access device 20 can be packaged pre-assembled as shown in FIGS. 1A and 1B, with the guidewire 28 coaxially disposed within the needle 20, the guide wire hub 46 secured to the track 30, the needle coaxially disposed within the dilator 24, the needle hub 34 locked to the dilator hub 38, the guidewire track 30 attached to the dilator hub 38, the dilator 24 coaxially disposed within the sheath 26, and the dilator hub 38 locked to the sheath hub 42. In some alternative embodiments, the splittable sheath 26A is packaged uncoupled from the remainder of the access device 20. Prior to use, the physician or healthcare provider can insert the needle body 32 and dilator body 36 into the sheath 36A, and advance the needle and dilator distally or the sheath proximally relative to one another until the sheath hub 42 locks to the dilator hub 38.

Figure 7C:
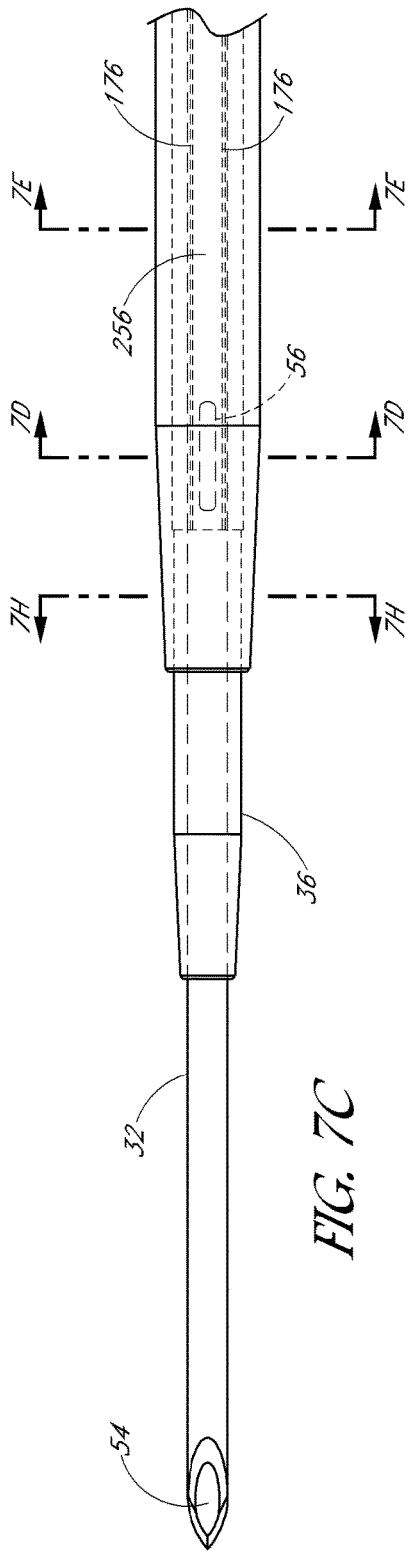
FIG. 7C is an enlarged view of a portion of the embodiment depicted in FIG. 8B and illustrates a needle opening in hidden lines.
Figure 7E:
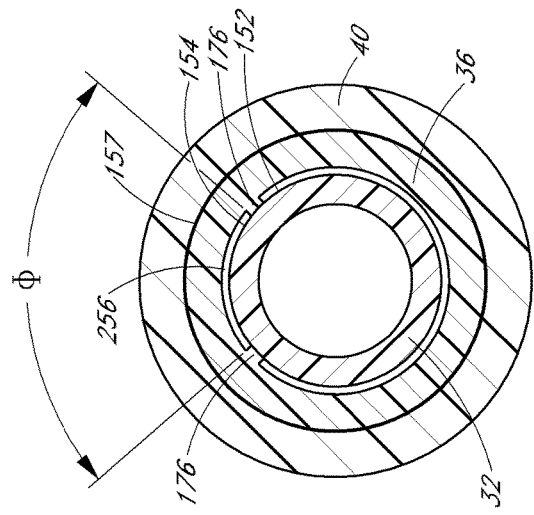
FIG. 7E is an enlarged cross-sectional view of the embodiment depicted in FIG. 7C proximal to the needle opening along line 7E-7E.
Figure 7D:
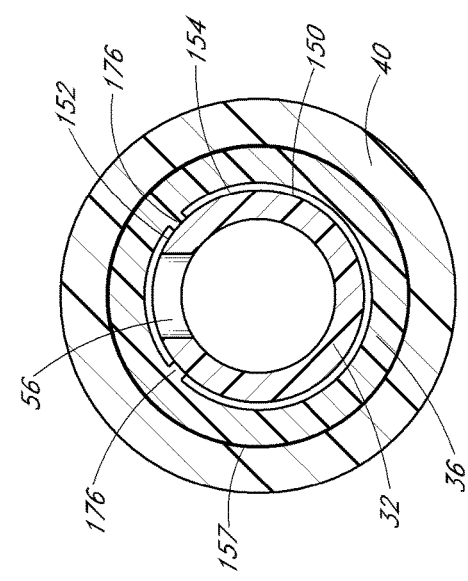
FIG. 7D is an enlarged cross-sectional view of a portion of the embodiment depicted in FIG. 7C and shows the needle opening or fenestration so as to allow fluid to flow from inside the needle to a channel formed between the needle and dilator.

In use, the needle body 32 is inserted into a blood vessel 148 or other body site as shown in FIGS. 7A-7B. FIGS. 7C-7E illustrate an embodiment of the access device at this stage of use, wherein a channel is formed between the needle and the dilator, to allow, for example, blood to flow during a blood flash. Referring to FIGS. 7C-7G, the needle body 32 includes one or more fenestrations 56 that allow blood to flow through the sidewall of the needle body 32 and into a space between the needle body 32 and the dilator shaft 36. One or more optional ridges 176 (e.g., two ridges 176 extending from the dilator shaft 36 are shown in the illustrated embodiment) can extend between the needle body 32 and the dilator shaft 36. The ridges 176 can define the sides of at least one channel 256 extending along a length of the needle body 32. In some embodiments additional channels 256 can be formed with additional ridges or other features. In some embodiments, the ridges 176 can include longitudinal gaps, to allow circumferential or transverse flow between adjacent channels formed by the ridges 176. In other embodiments channels 256 can be formed with a protruding ridge, or without a protruding ridge such as with a depression(s) or with a concentric gap. Channel 256 can be formed with protruding ridges (as shown) or non-protruding recessed grooves or flowpaths on the inner surface of the dilator shaft 36 and/or the outer surface of the needle body 32. Channel 256 can be formed without protruding ridges and/or grooves, and can simply comprise the annular space formed between needle body 32 and dilator shaft 36. Although the channel 256 is depicted as straight, it can also form other patterns such as a helix or another shape wrapping about the access device. Further, where multiple channels are present they can form intersecting helices, parallel helices, or other patterns. In other embodiments, a distance between the needle body 32 and a dilator shaft 36 (e.g. where the inner diameter of the dilator shaft exceeds the outer diameter of the needle body) can generally define a space, or a generally annular space, similar to the space created by the channels 256.

In some embodiments, the access device 20 includes features to vent the flash channel 256. Examples of various vents can be found in PCT International Patent Application No. PCT/US2012/051495, filed Aug. 17, 2012, which is incorporated by reference in its entirety herein. In some embodiments, venting can be provided at least partially through an insert 51 between the dilator hub 38 and needle hub 34, as shown in FIGS. 7I-7K. In some embodiments, an additional piece such as the insert 51 can facilitate the provision of certain desirable dimensions, materials, and other design features that might not be otherwise possible or economical. For example, it may be desirable for a middle portion of the dilator shaft 36 to have an inner diameter substantially larger than the outer diameter of the needle body 32 near a needle fenestration. This difference in diameters can create a space that allows a body fluid to flow between the two (such as in the channel 256) from the fenestration. However, in some embodiments it may also be desirable to provide the dilator shaft 36 with a smaller inner diameter near the dilator's distal tip. In further embodiments it may be desirable to provide a proximal portion of the dilator 424 that also has a smaller diameter to hinder the flow of a body fluid such as blood proximally while still allowing the venting of gases. This venting can facilitate the drawing of a body fluid into the space, cavity, or channel. However, it may be difficult to manufacture a dilator 24 with small inner diameters at its proximal and distal ends, and a large inner diameter in a middle portion.

The embodiment depicted in FIGS. 7I-7K provides venting with the assistance of an insert 51. The insert 51 can be disposed within a proximal opening 107 of the dilator hub 38. The proximal opening 107 can be configured to also receive a distally protruding portion 109 of the needle hub 34. In some embodiments the insert 51 can be press-fit into the dilator hub 38, while in other embodiments it can be loosely slid onto the needle body 32 (e.g., prior to combination with the dilator).

As best depicted in FIG. 7K, the insert 51 defines a through-hole 101 that can slidingly receive the needle 22 (or another needle described herein), e.g. along the needle body 32. Further, as depicted, the insert 51 can be substantially circular, or donut-shaped, allowing flexibility in its rotational position within the dilator hub 38. However, in other embodiments the insert 51 can be rotationally fixed within the dilator hub 38, i.e., with a non-circular insert and a corresponding non-circular receiving portion in the dilator hub 38.

Even further, the insert 51 can have particular dimensions to facilitate the release of gases while hindering the release of body fluids. For example, the diameter of the insert's through-hole 101 can be only slightly greater than the outer diameter of the needle body 32, creating a space or gap (not shown) between insert 51 and needle body 32, the gap sized to allow the release of gases but hinder the release of a body fluid. As best shown in FIGS. 7I and 7J, the gases can then flow proximally within the gap between insert 51 and needle body 32 and enter a space 107, 108 between the needle hub 34 and the insert 51 within the receiving portion or opening 107 of the dilator hub 38. From this space, the gases can then proceed to the ambient atmosphere in a passage 111 defined between the needle hub 34 and the dilator hub 38. Notably, although in some embodiments the needle hub 34 and the dilator hub 38 can connect via a luer connection that may prevent the passage of gases, additional mechanisms known in the art or described herein can also attach the two hubs. For example, in the depicted embodiment the needle hub 34 can include latch element 66 that can releasably hook to a ledge portion or lip 77 of the dilator hub 38. Thus, components that might otherwise form a luer connection between the two hubs can also be sufficiently separated to allow the escape of gases without compromising a connection between the hubs.

Further, the outer edge of the insert 51 can be shaped to substantially match the receiving portion of the receiving portion of the dilator hub 38 to form a seal between the two that at least hinders the escape of a body fluid therethrough. In some embodiments, a taper 105 within the dilator hub 38 (also used for a luer connection with a needle, as discussed above) can facilitate a seal between the insert 51 and the dilator hub. In some embodiments, the seal between the outer edge of the insert 51 and the receiving portion 107 of the dilator hub 38 can also be impermeable to gases, forcing their passage through the through-hole 101, as described above.

The insert 51 can also include a proximally projecting portion depicted as a ridge 103 along its proximal face, which can be of particular relevance as shown in FIG. 7J. For example, if the insert 51 is askew, it may not completely insert into the dilator hub 38, leaving a gap 106 between the insert 51 and a distal portion of dilator hub 38 within opening 107, as depicted in FIG. 7J. Gap 106 could allow the insert 51 to come into contact with the needle hub 34, potentially forming a seal, preventing the escape of gases through the insert's through-hole 101. Thus, in some embodiments, the insert can also include a ridge 103 with one or more grooves 104. The needle hub 34 can contact the ridge 103 before contacting the rest of the proximal end of the insert 51, preserving a space therebetween. The one or more grooves 104 provide an opening or channel in the ridge 103 for gases to pass through, to the passage 111 between the hubs 34, 38. In the depicted embodiment, more than one groove can be provided to advantageously allow gases to pass through in multiple directions. Thus, if sealing contact between the insert 51 and the needle hub 34 is made on one side, gases can still escape on the other side.

The blood flash channel 256 can have various thicknesses and span angles. The thickness of the channel 256 can vary depending on the dimensions of the needle 22 and dilator 24. The channel 256 can have a span angle Φ about the axis of the dilator 24 of about 30 degrees to about 210 degrees or more, but preferably less than 360 degrees. More preferably, the channel 256 can have a span angle (Φ) of about 60 to 150. In the illustrated embodiment, the channel 256 spans 120 degrees. The thickness and span angle Φ can be chosen so as to optimize the capillary action that occurs within the channel 256 as fluid (e.g., whole blood) enters the channel 256 as may further be selected based on the expected pressure in the body cavity and viscosity of the liquid. Various graphs of test data illustrating how quickly a fluid is drawn up the surfaces of a channel within an access device are disclosed in PCT International Patent Application No. PCT/US2011/024097, filed Feb. 8, 2011, which is incorporated by reference in its entirety herein.

The shape of the channel 256 described above and the resulting capillary action were optimized for use with whole blood as opposed to other fluids having a different viscosity than whole blood (e.g. leukocytes, pus, urine, plasma). However, the shape of the channel 256 is not limited to the disclosed shape and may be optimized for draining other liquids, such as pus. Further, the shape of the channel 256 described above was optimized for peripherally located vessels where the pressure in the vessel enhances the capillary action and resulting blood flash as well as for vessels located in the regions where the pressure may be low. For example, in the thorax region of the body, the expected pressure in the veins may be lower than in a peripherally located vein when the patient breathes. A different size of the channel for use of the access device 20 in other regions of the body may be employed taking into account the expected pressure within the vessel or body cavity.

Figure 7H:
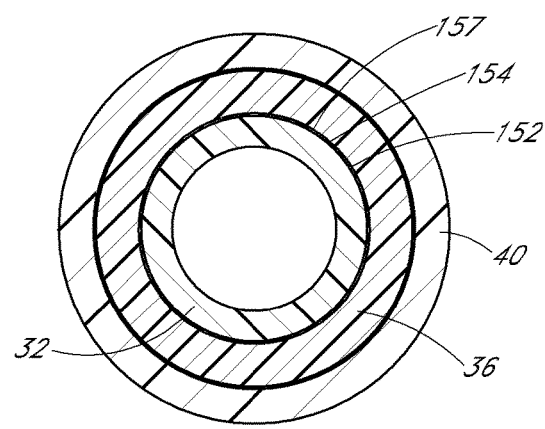
FIG. 7H is an enlarged cross-sectional view of the embodiment depicted in FIG. 7C distal to the needle opening along line 7H-7H.
Figure 7I:
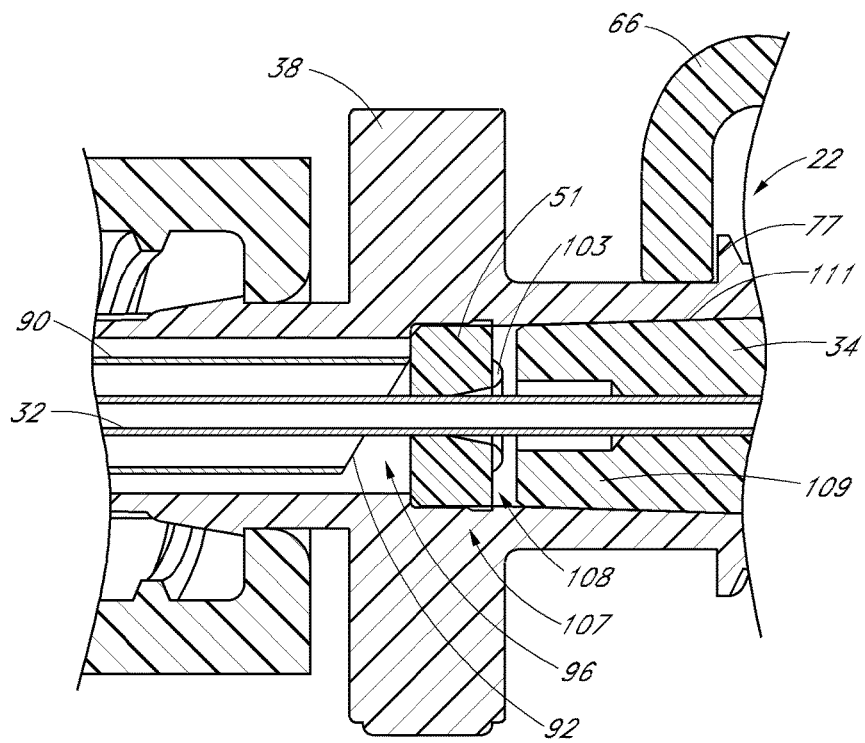
FIG. 7I is an enlarged cross-sectional view of another embodiment of an access device showing portions of a needle hub, a dilator hub, and an insert.
Figure 7J:
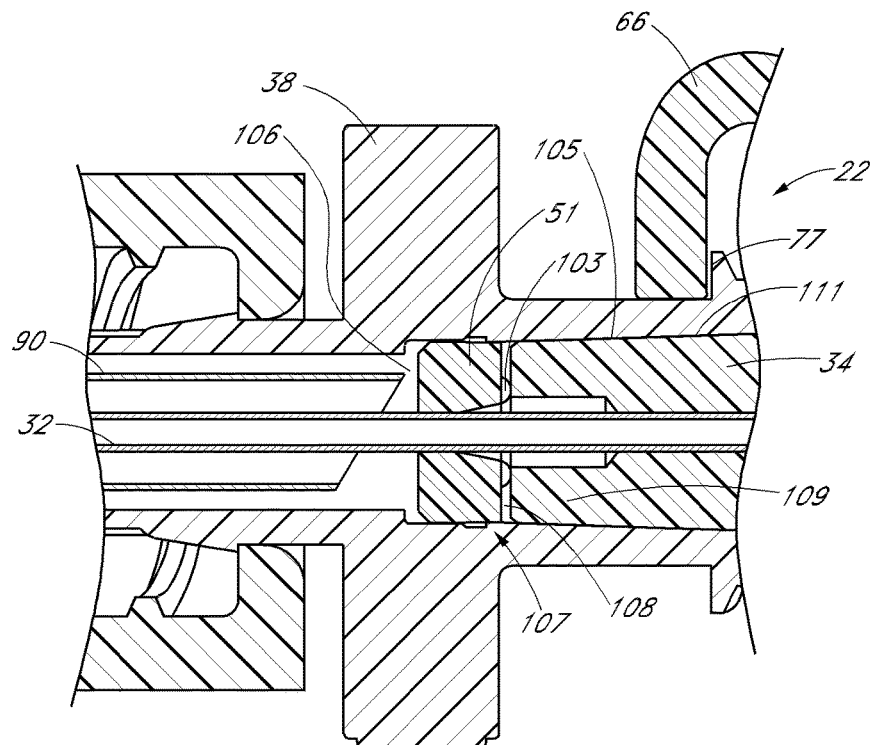
FIG. 7J is an enlarged cross-section view of the access device of FIG. 7I, wherein an insert is not fully inserted.
Figure 7K:
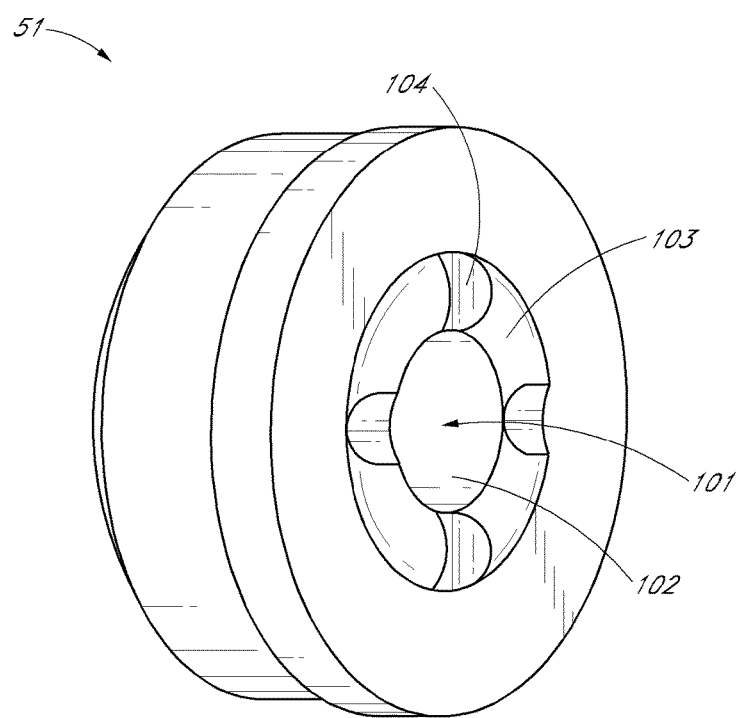
FIG. 7K is an enlarged view of an insert of the access device of FIG. 7I.

With reference to FIG. 7H, in a region of the access device 20 distal of fenestration 56, the dilator shaft 36 is coaxially positioned to minimize an annular space 157 between the needle body 32 and the dilator shaft 36 while still allowing relative movement of the needle body 32 and the dilator shaft 36. The inner surface 152 of the dilator shaft 36 need not, though it can, lie directly against the outer-surface 154 of the needle body 32. The annular interface 157 between the outer-surface 154 of the needle body 32 and the inner surface 152 of the sheath dilator shaft 36 may be reduced in this region to inhibit the distal flow of blood or its constituents (or other fluids) from the opening 56 in the needle body 32.

Figures 8A, 8B:
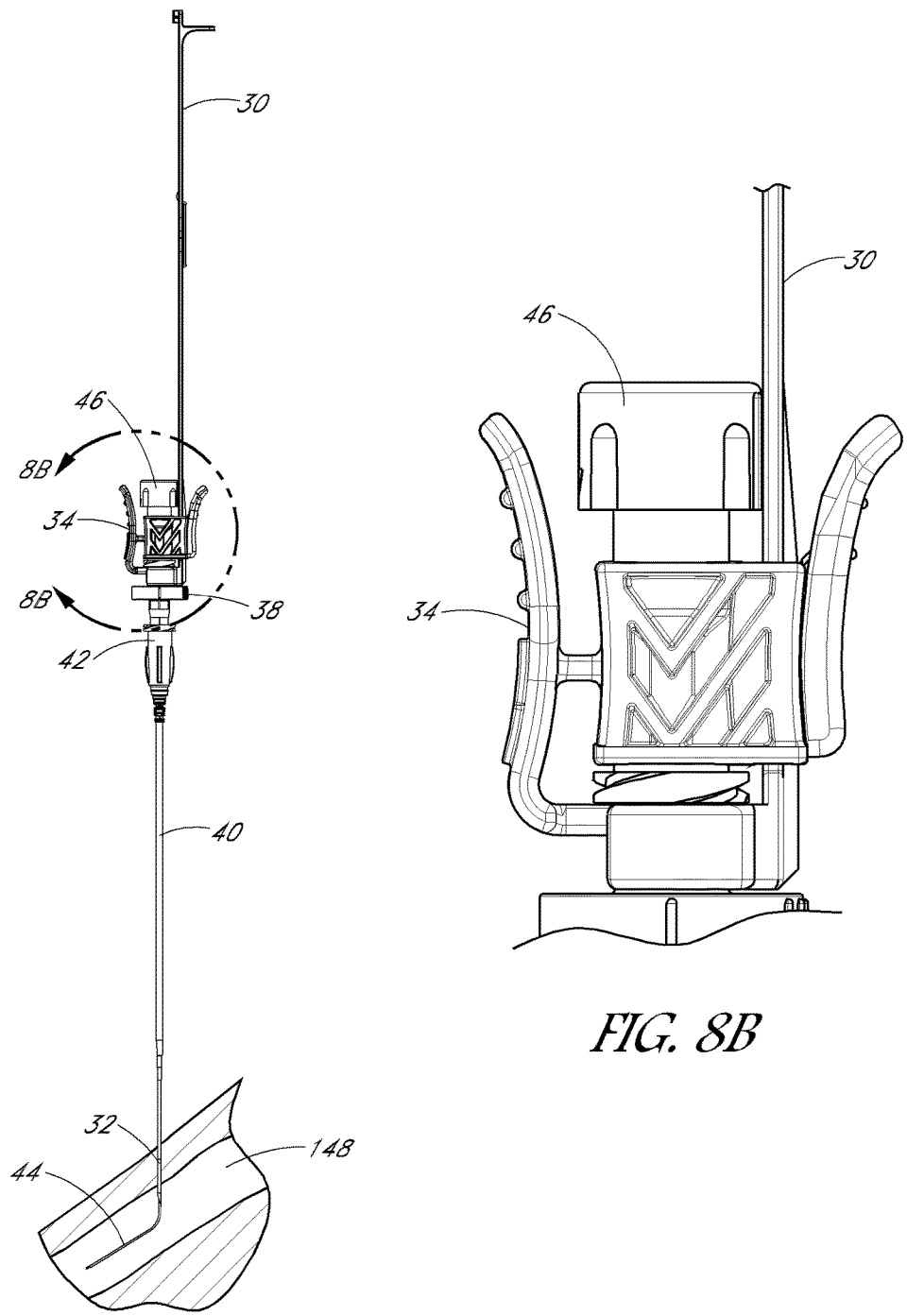
FIG. 8A is a side view of the embodiment depicted in FIG. 1A illustrating the guidewire advanced from the needle tip in a distal direction.
FIG. 8B is an enlarged view of the embodiment depicted in FIG. 8A focusing on the area where the guidewire hub is locked to the needle hub when the needle hub is in the first position.
Figures 10A, 10B:
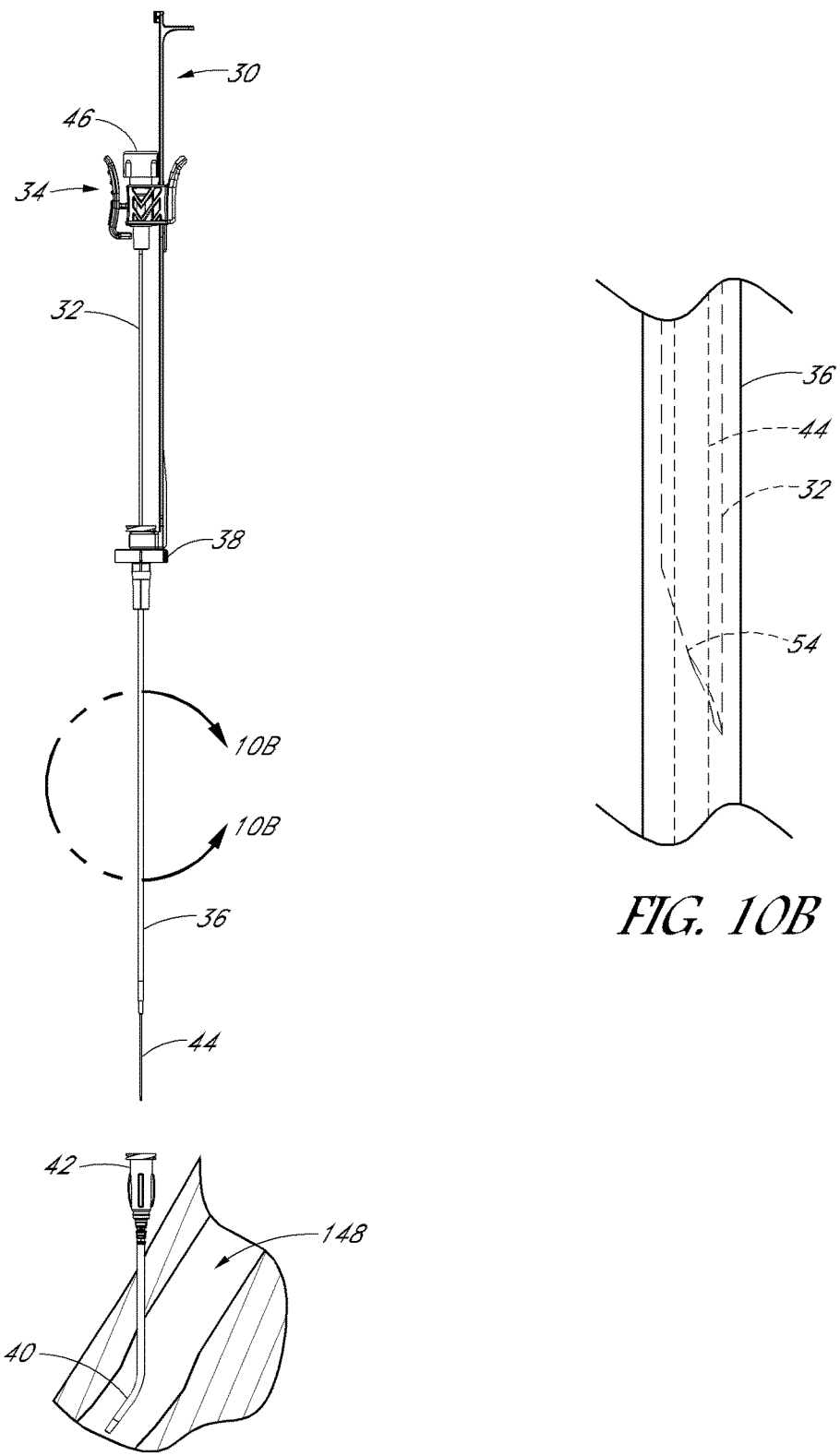
FIG. 10A is a side view of the embodiment depicted in FIG. 1A illustrating the removal of the guidewire, needle body, and dilator from the sheath.
FIG. 10B is an enlarged view of the portion of the embodiment illustrated in FIG. 10A showing the needle tip covered by the dilator during removal of the guidewire, needle body, and dilator from the sheath.

With reference to FIGS. 8A-8B, once the physician or healthcare provider has located the needle 22 within the target blood vessel, the guidewire 44 is inserted into the vessel 148 by advancing the guidewire hub 46 distally until the guidewire hub 46 locks to the needle hub 34. Next, the dilator body 36 and sheath body 40 are inserted into the vessel 148 by releasing the dilator hub 38 from the needle hub 34 and advancing the dilator 24 and sheath 26 distally relative to the needle hub 34 along the guidewire and needle as shown in FIGS. 9A-9B. The guidewire track 30 also advances distally with the dilator hub 38, and the needle hub 34 locks to the locking mechanism 128 of the track 30, preventing further movement of the needle hub 34. With reference to FIGS. 10A-10B, the guidewire 44 and dilator body 36 are removed from the vessel 148 leaving the sheath body 40 properly inserted within the vessel 148.

For a physician or healthcare provider relying on blood flash to confirm that the needle 22 has punctured a blood vessel, it is important for the blood flash to be visible and noticeable as soon as possible upon entry into the blood vessel. Due to the relatively small diameter of peripheral blood vessels, even a small delay in the appearance of the blood flash can result in the physician continuing to advance the needle 22, possibly completely through the blood vessel. In some cases, a larger flash channel 256 (e.g., one associated with a larger French dialator) can result in a slower blood flash because blood entering the channel 256 has a larger volume to fill before traveling proximally along the outer surface of the needle. Various parameters, including the dimensions of the various components of the access device 20, can affect the size of the flash channel 256 and speed of the blood flash. A physician or healthcare professional may want to place a relatively large sheath 26 in the vessel 148 in certain circumstances, for example, to deliver a large volume of fluid rapidly, to introduce other devices or instruments into the vessel 148 via the sheath 26 (e.g., introduce a Central Vascular Catheter (CVC)), to remove fluid or specimens from the vessel 148, or various other reasons. Therefore, some access devices 20 include a relatively larger sheath 26 and therefore a relatively larger dilator 24, which can result in a larger flash channel 256 for a given size of needle. For example, in an access device 20 having a 21 gauge needle body 32 and a 7 French dilator 24, a distance $d_1$ between an outer diameter of the needle body 32 and an inner diameter of the dilator 24 can be about 0.025 inches (in.). The dimension $d_1$ of this magnitude corresponds to a larger than conventional cross-sectional surface area which can result in a blood flash that is slower than desired.

Figure 11A:
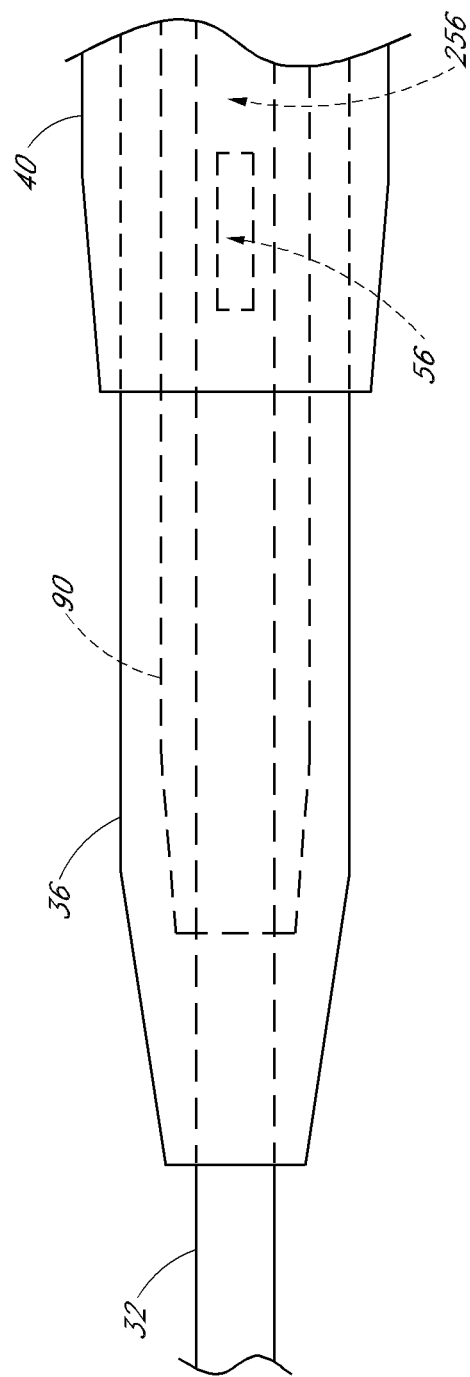
FIG. 11A is a partial side view of an embodiment of an access device including an inner member.
Figure 11B:
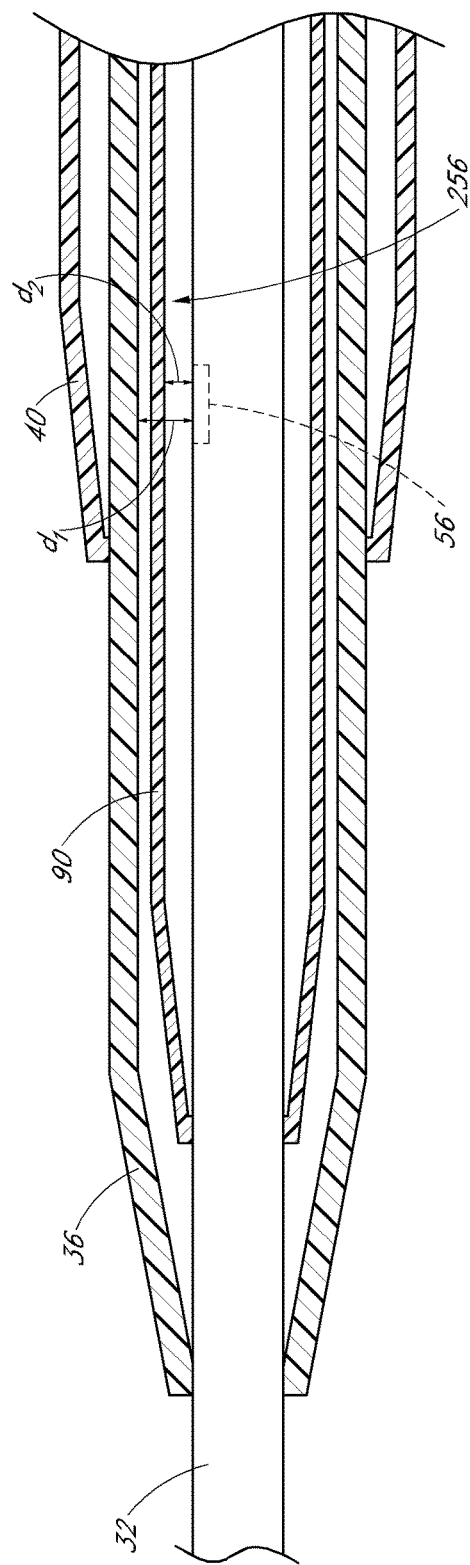
FIG. 11B is a partial section view of the access device of FIG. 11A.

To reduce the size of the flash channel 256 and produce a faster blood flash, the access device 20 can include an inner member 90, that is coaxially disposed between the needle body 32 and dilator shaft 36, for example as shown in FIGS. 11A and 11B, and that displaces blood or other body fluids between the needle body 32 and the dilator shaft 36. A distal end of the inner member 90 is proximal to a distal end of the dilator shaft 36, but distal to the fenestration 56 in the needle body 32. The inner member 90 can be positioned coaxially with the dilator shaft 36. In particular, the inner member 90 can occupy some of the volume defined between the inner surface of the dilator 36 and the outer surface of the needle body 32. The inner member 90 reduces the free volume between these components to expedite the flash and, in some embodiments, defines a smaller flash volume between the needle body 32 and the inner member 90. In a region of the access device distal of fenestration 56, the inner member 90 can reduce and in some cases minimize an annular space between the needle body 32 and the inner member 90. An inner surface of a distal end portion of the inner member 90 need not, though it can, lie directly against the outer surface of the needle body 32. In a preferred form, the distal end of the inner member 90 defines an orifice through which the needle body 32 passes in a manner of slip fit or slight interference fit. An annular interface between the outer surface of the needle body 32 and the inner surface of the inner member 90 may be reduced in this region to inhibit the distal flow of blood or its constituents (or other fluids) from the opening 56 in the needle body 32.

In embodiments of the access device including the inner member 90, the flash channel 256 is formed between the needle body 32 and the inner member 90 rather than between the needle body 32 and an inner surface of the dilator shaft 36, thereby reducing the cross-sectional area of, e.g., the dimension of, the flash channel 256 from $d_1$ to $d_2$ as indicated in FIG. 11B. In some embodiments, the inner member 90 can reduce the thickness of the flash channel 256 to about one half or less than about one half, for example, about one fifth, about one tenth, or less than one tenth, of the thickness of the flash channel 256 without the inner member 90. In some embodiments of the access device having a 21 gauge needle body 32 and a 7 French dilator 24, the presence of the inner member 90 can reduce the thickness of the flash channel 256 from about 0.025 in. to between about 0.003 in. and about 0.005 in.

Figure 12:
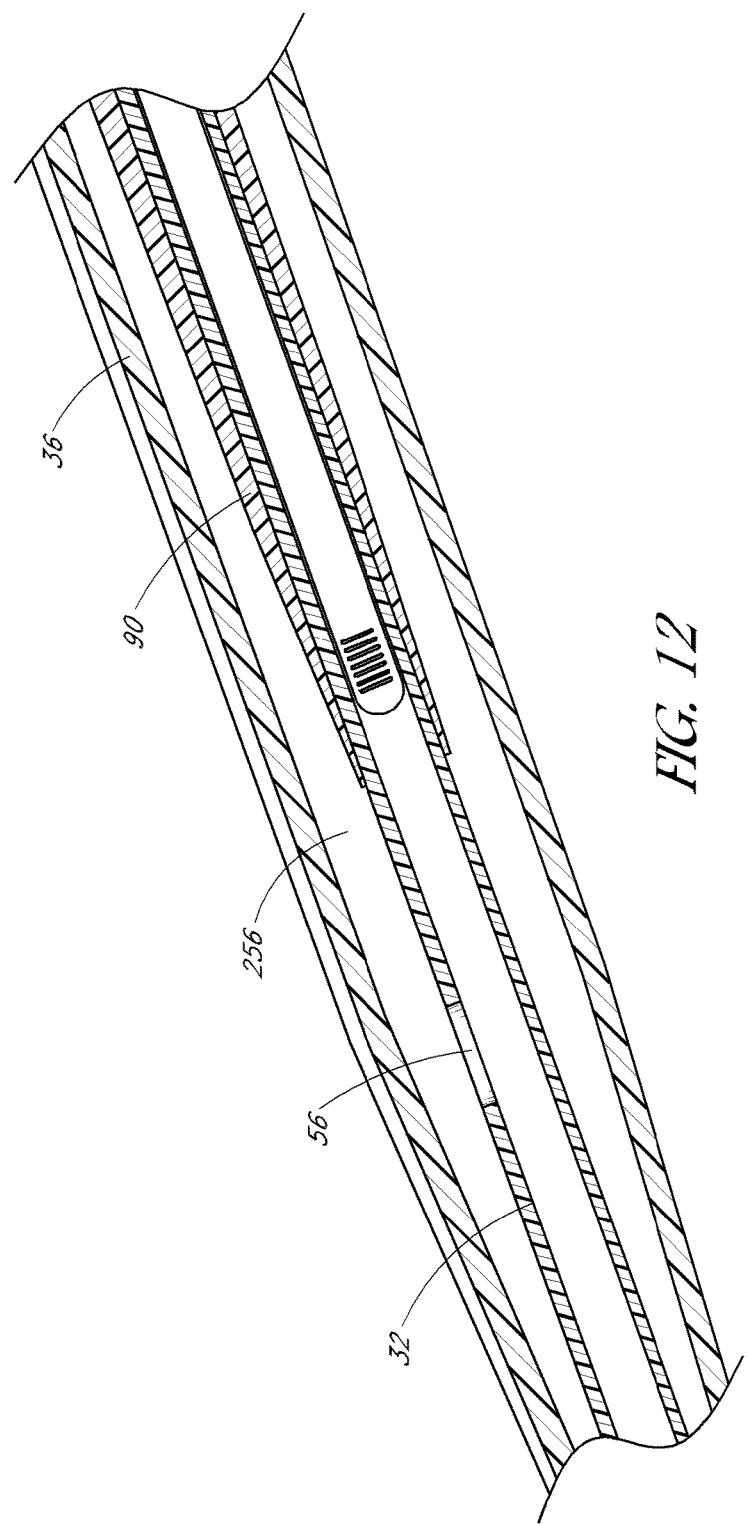
FIG. 12 is a perspective view of an embodiment of an access device including an inner member.

In some alternative embodiments, the distal end of the inner member 90 is proximal to both the distal end of the dilator shaft 36 and to the fenestration 56 in the needle body 32 so that the fenestration 56 is between the distal end of the inner member 90 and the distal end of the dilator shaft 36, for example as shown in FIG. 12. In such embodiments, the flash channel 256 is formed between the inner member 90 and the dilator 24.

In some embodiments, an access device including the inner member 90 can also include an insert 51 as described herein. The insert 51 can allow for easier assembly of the access device, help keep the inner member 90 in place, provide venting of the space between the needle body 32 and the inner member 90 and/or the space between the inner member 90 and the dilator shaft 36, and/or help prevent blood from passing proximally out of the flash channel 256.

The space between the inner member 90 and the dilator shaft 36 can be, but need not be, in communication with the space between the inner member 90 and the needle body 32. Communication between these spaces can be accomplished in a number of ways. In some embodiments, a proximal end of the inner member 90 can have a bias cut edge 92, and the long point of the bias cut edge can abut the insert 51 when the insert 51 is fully seated in the dilator hub 38, as shown in FIG. 7I. The bias cut leaves a gap 96 between the remainder of the proximal edge of the inner member 90 and the insert 51 to advantageously allow venting of the flash channel 256 between the needle body 32 and inner member 90. In some embodiments, one or more spacer or standoff members can be disposed between portions of the proximal end of the inner member 90 and the insert 51 to maintain one or more gaps to allow for venting. The spacer or standoff member(s) can be separate from or integrally formed with one or both of the inner member 90 and insert 51. In some embodiments, the proximal edge of the inner member 90 fully abuts and/or is integral with the insert 51. In some such embodiments, the inner member 90 includes one or more fenestrations and/or reliefs to provide fluid communication.

In some embodiments, the access device can be assembled by sliding the insert 51 onto the needle body 32, inserting the needle body 32 into the inner member 90, and inserting the combination of the needle body 32 and the inner member 90 into the dilator 24. A proximal portion of the inner member 90 can extend into the dilator hub 38 when assembled as shown in FIGS. 7I and 7J. When assembled, the inner member lies within the dilator shaft 36 with its distal end fit onto the needle body 32. The distal end of the dilator body 36 prevents distal movement of the inner member 90 beyond the dilator 24. And the insert 51 prevents proximal movement of the inner member 90 beyond the dilator 24.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above.

What is claimed is:

1. A splittable sheath comprising:
   a splittable sheath body comprising a generally flexible tubular structure, a proximal end, and a distal end, the sheath body defining a longitudinal axis and being splittable into two portions along a pre-determined line generally parallel to the longitudinal axis;
   a splittable sheath hub extending from the proximal end of the sheath body defining a longitudinal axis generally aligned with the longitudinal axis of the sheath body, the sheath body and sheath hub forming an inner cavity along their respective longitudinal axes; and
   a valve element comprising:
      a resilient plate comprising a sealing portion extending radially inwardly from a side of the inner cavity;
      a sealing element comprising a domed first sealing surface and being supported by the resilient plate such that the sealing element is biased toward a position against a second sealing surface to substantially seal the inner cavity; and
      an annular member comprising the second sealing surface, the annular member having a central bore and a tapered surface that slopes from an outer edge of the annular member to the central bore such that the annular member decreases in thickness from the outer edge to an inner edge of the annular member proximate to the central bore, the domed first sealing surface corresponding to the central bore of the annular member.

2. The splittable sheath of claim 1, wherein a lower portion of the annular member comprises the second sealing surface.

3. The splittable sheath of claim 1, wherein the sealing element comprises polyurethane.

4. The splittable sheath of claim 1, wherein the sealing element comprises polycarbonate.

5. The splittable sheath of claim 1, wherein the annular member is relatively softer than the sealing element.

6. The splittable sheath of claim 1, wherein the resilient plate being connected to only one of a two halves of the sheath hub and extending into the inner cavity.

7. The splittable sheath of claim 1, wherein the resilient plate is configured to move between a first position and a second positon, the resilient plate when in the first positon extends substantially perpendicular to a longitudinal axis of the inner cavity and blocks fluid flow through the inner cavity in at least one direction, the resilient plate when in the second position bends about an axis that is transverse to the longitudinal axis of the inner cavity.

8. A splittable sheath comprising:
   a splittable sheath body comprising a generally flexible tubular structure, a proximal end, and a distal end, the sheath body defining a longitudinal axis;
   a splittable sheath hub coupled with the proximal end of the sheath body, the sheath body and the hub having aligned openings forming a passage therethrough; and
   a valve comprising:
      an annular member disposed against a surface of the hub facing the sheath body, the annular member having and opening therethrough disposed in the passage; and
      a sealing member having an engagement portion coupled with a structure of the sheath assembly disposed generally between the surface of the hub and the distal end of the sheath body, and a seal portion projecting into sealing engagement with the opening in the annular member in a sealing position and disposed away from the opening in the annular member in an open position.

9. The splittable sheath of claim 8, wherein the valve further comprises a resilient plate coupled with the sealing member, the plate extending radially inwardly from a side of an inner cavity of the sheath assembly.

10. The splittable sheath of claim 9, wherein the sealing member comprises a domed first sealing surface and being supported by the resilient plate such that the sealing member is biased toward a position against the annular member to substantially seal the inner cavity.

11. The splittable sheath of claim 10, wherein the domed first sealing surface comprises polycarbonate.

12. The splittable sheath of claim 9, wherein the sheath hub has two halves, and the resilient plate is connected to only one of the two halves of the sheath hub and extends into the inner cavity.

13. The splittable sheath of claim 9, wherein the resilient plate is configured to move between a first position and a second positon, the resilient plate when in the first positon extends substantially perpendicular to a longitudinal axis of the passage and blocks fluid flow through the passage in at least one direction, the resilient plate when in the second position bends about an axis that is transverse to the longitudinal axis of the passage.

14. The splittable sheath of claim 9, wherein the engagement portion is configured to move between a first position and a second positon, the engagement portion when in the first positon extends substantially perpendicular to a longitudinal axis of the passage and blocks fluid flow through the passage in at least one direction, the engagement portion when in the second position bends about an axis that is transverse to the longitudinal axis of the passage.

15. The splittable sheath of claim 10, wherein a lower portion of the annular member comprises a second sealing surface.

16. The splittable sheath of claim 8, wherein the annular member comprises an O-ring.

17. The splittable sheath of claim 8, wherein the annular member is tapered from a top surface thereof to decrease in thickness from an outer portion toward the opening therein.

18. The splittable sheath of claim 8, wherein the splittable sheath is splittable into two portions along a pre-determined line generally parallel to the longitudinal axis.

19. The splittable sheath of claim 8, wherein the annular member comprises an O-ring.

20. A splittable sheath comprising:
a splittable sheath body comprising a generally flexible tubular structure, a proximal end, and a distal end, the sheath body defining a lumen along a longitudinal axis;
a splittable hub coupled with the proximal end of the sheath body and having a passage therethrough; and
a soft polymeric diaphragm coupled with a distal face of the hub providing fluid communication between the lumen and the passage when open and having a proximal face configured to seal against a device disposed in the passage, diaphragm and lumen of the sheath assembly.

21. The splittable sheath of claim 20, further comprising a sealing member having an engagement portion coupled with a structure of the sheath assembly disposed generally between the surface of the hub and the proximal end of the sheath body, and a seal portion projecting into sealing engagement the opening in the annular member in a sealing position and disposed away from the opening in the annular member in an open position.

22. The splittable sheath of claim 21, wherein the sheath hub has two halves, and the engagement portion is connected only to one of the two halves of the sheath hub and extends into the inner cavity.

23. The splittable sheath of claim 21, wherein the seal portion comprises polycarbonate.

\* \* \* \* \*